US012027267B2

(12) United States Patent
Kikuchi et al.

(10) Patent No.: US 12,027,267 B2
(45) Date of Patent: Jul. 2, 2024

(54) INFORMATION PROCESSING APPARATUS, INFORMATION PROCESSING SYSTEM, INFORMATION PROCESSING METHOD, AND NON-TRANSITORY COMPUTER-READABLE STORAGE MEDIUM FOR COMPUTER-AIDED DIAGNOSIS

(71) Applicant: CANON KABUSHIKI KAISHA, Tokyo (JP)

(72) Inventors: Toru Kikuchi, Hino (JP); Kiyohide Satoh, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 151 days.

(21) Appl. No.: 16/700,939

(22) Filed: Dec. 2, 2019

(65) Prior Publication Data

US 2020/0105414 A1    Apr. 2, 2020

Related U.S. Application Data

(63) Continuation of application No. PCT/JP2018/020472, filed on May 29, 2018.

(30) Foreign Application Priority Data

Jun. 5, 2017  (JP) .................. 2017-111068

(51) Int. Cl.
*G16H 50/20* (2018.01)
*G16H 30/20* (2018.01)
*G16H 50/70* (2018.01)

(52) U.S. Cl.
CPC ............. *G16H 50/20* (2018.01); *G16H 30/20* (2018.01); *G16H 50/70* (2018.01)

(58) Field of Classification Search
CPC ......... G16H 30/20; G16H 50/70; G16H 50/20
See application file for complete search history.

(56) References Cited

U.S. PATENT DOCUMENTS

| 2004/0122790 | A1* | 6/2004 | Walker | ................ G16H 30/40 |
| 2010/0135552 | A1* | 6/2010 | Leib | ................... G16H 30/20 |
| | | | | 382/128 |
| 2016/0110632 | A1* | 4/2016 | Kiraly | ................ G06V 10/267 |
| | | | | 382/128 |

(Continued)

FOREIGN PATENT DOCUMENTS

| JP | 2009-093582 A | 4/2009 |
| JP | 2017-504087 A | 2/2017 |
| WO | 2017/017722 A1 | 2/2017 |

OTHER PUBLICATIONS

Kim et al., X-Ray Image Classification Using Random Forests With Local Binary Patterns, Proceedings of the Ninth International Conference on Machine Learning and Cybernetics, Qingdao 3190-3194 (Jul. 2010) (Year: 2010).*

(Continued)

*Primary Examiner* — Jordan L Jackson
(74) *Attorney, Agent, or Firm* — Canon U.S.A., Inc., IP Division

(57) ABSTRACT

An information processing apparatus is configured to acquire case information containing first information that is information on a feature of a case of a patient and that is obtained as a result of a diagnosis of the patient and determine, based on the first information that is the information contained in the case information, whether the case information is used as training data for machine training.

20 Claims, 13 Drawing Sheets

(56) References Cited

U.S. PATENT DOCUMENTS

| | | | |
|---|---|---|---|
| 2016/0203263 A1* | 7/2016 | Maier | G06T 7/0016 705/2 |
| 2016/0283680 A1* | 9/2016 | Deng | G16H 50/20 |
| 2016/0350919 A1* | 12/2016 | Steigauf | G06V 10/82 |
| 2016/0357936 A1* | 12/2016 | Ghouri | G06N 3/08 |
| 2016/0364526 A1* | 12/2016 | Reicher | G06T 7/0014 |
| 2016/0364862 A1* | 12/2016 | Reicher | G16H 15/00 |
| 2017/0018075 A1* | 1/2017 | Middlebrooks | G06N 20/10 |
| 2017/0046839 A1* | 2/2017 | Paik | G06K 9/6296 |
| 2017/0076043 A1* | 3/2017 | Dormer | G16H 40/67 |
| 2017/0076451 A1* | 3/2017 | Pauly | G16H 50/20 |
| 2018/0232603 A1* | 8/2018 | Shim | A61B 6/00 |
| 2021/0065900 A1* | 3/2021 | Douglas | G16H 50/20 |

OTHER PUBLICATIONS

Mohd S. Baba, Multilevel feature extraction and Xray image classification 7(8) J of Applied Sciences 1224-1229 (Year: 2007).*

Marleen de Bruijne, Machine learning approaches in medical image analysis: From detection to diagnosis, 33 Medical Image Analysis 94-97 (Year: 2016).*

Pranckevičius and Marcinkevičius, Comparison of Naïve Bayes, Random Forest, Decision Tree, Support Vector Machines, and Logistic Regression Classifiers for Text Reviews Classification, 5(2) Baltic J Modern Computing 221-232 (Jan. 2017) (Year: 2017).*

Beaulieu-Jones et al., Semi-supervised learning of the electronic health record for phenotype stratification, 64 J of Biomedical Informatics 168-178 (Year: 2016).*

Parsazad et al., Data Selection for Semi-Supervised Learning, 9(2) International J of Computer Sciences 195-200 (Mar. 2012) (Year: 2012).*

Bianca Zadrozny, Learning and Evaluating Classifiers under Sample Selection Bias, Proceedings of the 21st International Conference on Machine Learning (Year: 2004).*

Koreen Millard and Murray Richardson, On the Importance of Training Data Sample Selection in Random Forest Image Classification: A Case Study in Peatland Ecosystem Mapping, 7 Remote Sensing 8489-8515 (Year: 2015).*

* cited by examiner

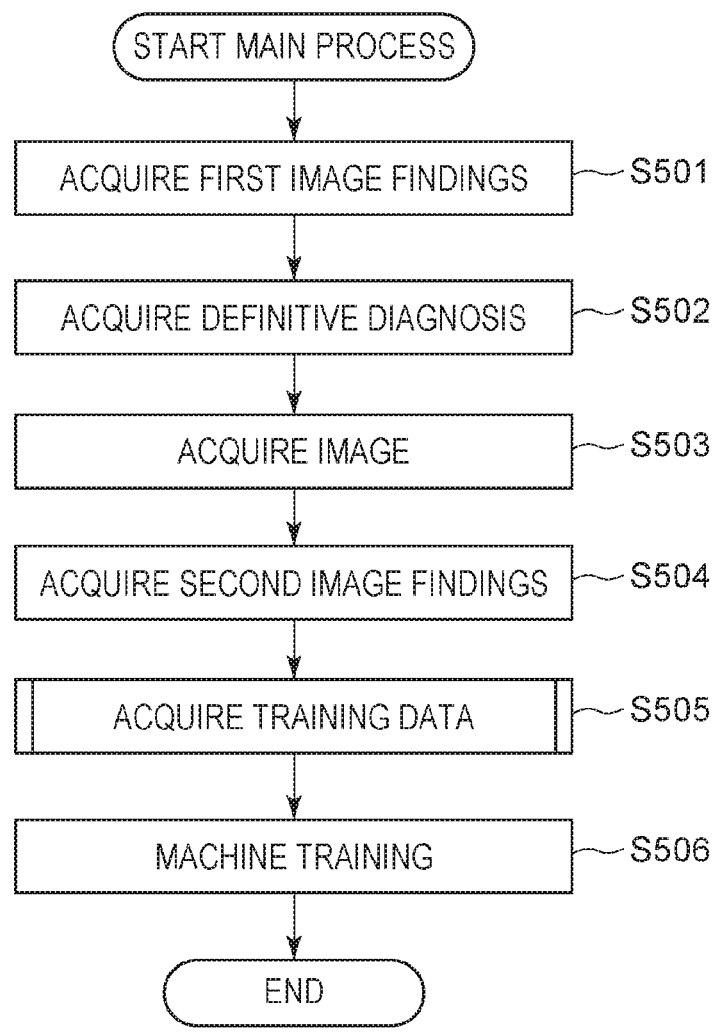

INFORMATION PROCESSING APPARATUS, INFORMATION PROCESSING SYSTEM, INFORMATION PROCESSING METHOD, AND NON-TRANSITORY COMPUTER-READABLE STORAGE MEDIUM FOR COMPUTER-AIDED DIAGNOSIS

CROSS-REFERENCE TO RELATED APPLICATIONS

This application is a Continuation of International Patent Application No. PCT/JP2018/020472, filed May 29, 2018, which claims the benefit of Japanese Patent Application No. 2017-111068, filed Jun. 5, 2017, both of which are hereby incorporated by reference herein in their entirety.

TECHNICAL FIELD

The present invention relates to an information processing apparatus, an information processing system, an information processing method, and a non-transitory computer-readable storage medium.

BACKGROUND ART

For health care professionals to make a determination in consideration of many pieces of information on the occasion of diagnosis or treatment, various computer-aided systems have been suggested. PTL1 describes extracting, from electronic documents containing the names of diseases of patients and findings on the diseases, elements of findings (finding elements) that compose the findings on the names of the diseases, based on the time-series frequencies of the electronic documents containing the finding elements.

CITATION LIST

Patent Literature

PTL1: Japanese Patent Laid-Open No. 2009-093582

Finding elements that are not contained in any electronic document cannot be extracted from an electronic document, and elements that have not been extracted cannot be included in data for training (training data).

SUMMARY OF INVENTION

An information processing apparatus according to an embodiment of the present invention includes a first acquiring unit configured to acquire case information containing first information, the first information being information on a feature of a case of a patient and being obtained as a result of a diagnosis of the patient, and a determining unit configured to determine, based on the first information, whether the case information is used as training data for machine training.

Further features of the present invention will become apparent from the following description of exemplary embodiments with reference to the attached drawings.

BRIEF DESCRIPTION OF DRAWINGS

FIG. 5 is a flowchart that shows an example of a process that is executed by the information processing apparatus according to the embodiments of the present invention.

DESCRIPTION OF EMBODIMENTS

Hereinafter, embodiments of the present invention will be described with reference to the drawings.

First Embodiment

A computer-aided diagnosis (CAD) system that provides information to aid doctors in determination by analyzing information obtained through diagnoses with a computer is known. Examples of the information obtained through diagnoses include pieces of information such as findings obtained through examinations, consultations, and observations of patients by doctors, medical images of the patients, and findings obtained by doctors through observations of the medical images. Findings obtained by doctors through examinations, consultations, and observations of patients include pieces of information such as the age and sex of patients and pieces of information such as examined data obtained through examinations, results of pathological diagnoses, anamneses, chief complaints, and diagnostic names determined by doctors or collegial systems of a plurality of doctors. Findings obtained by doctors through observations of medical images are information on features of tissues or lesions visualized into the medical images. Hereinafter, findings obtained by doctors through observations of medical images are referred to as image findings.

In the CAD system, a diagnostic name, or the like, for a new case can be inferred through machine training using information obtained in the past diagnoses. The quality of data that is used for training in machine training may be related to the accuracy of an inference that is inferred through machine training.

Here, the quality of data that is used for training is the amount and accuracy of information. That is, preferably, data that is used in machine training for the CAD system contains rich information and contains accurate information. Hereinafter, data that is used in machine training is referred to as training data. An information processing apparatus 101 according to the first embodiment is intended to perform machine training in the CAD system with high-quality training data.

Hereinafter, the case where the information processing apparatus 101 acquires training data for a CAD apparatus 102 that makes an inference on a chest disease based on image findings from chest X-ray computed tomography (CT) images captured from a patient as a subject will be described as an example. The information processing apparatus 101 acquires past image findings that are assigned to a case, acquired to be used as training data, and image findings that have not been acquired for the case by analyzing medical images of the case.

System Configuration

Figure 1:
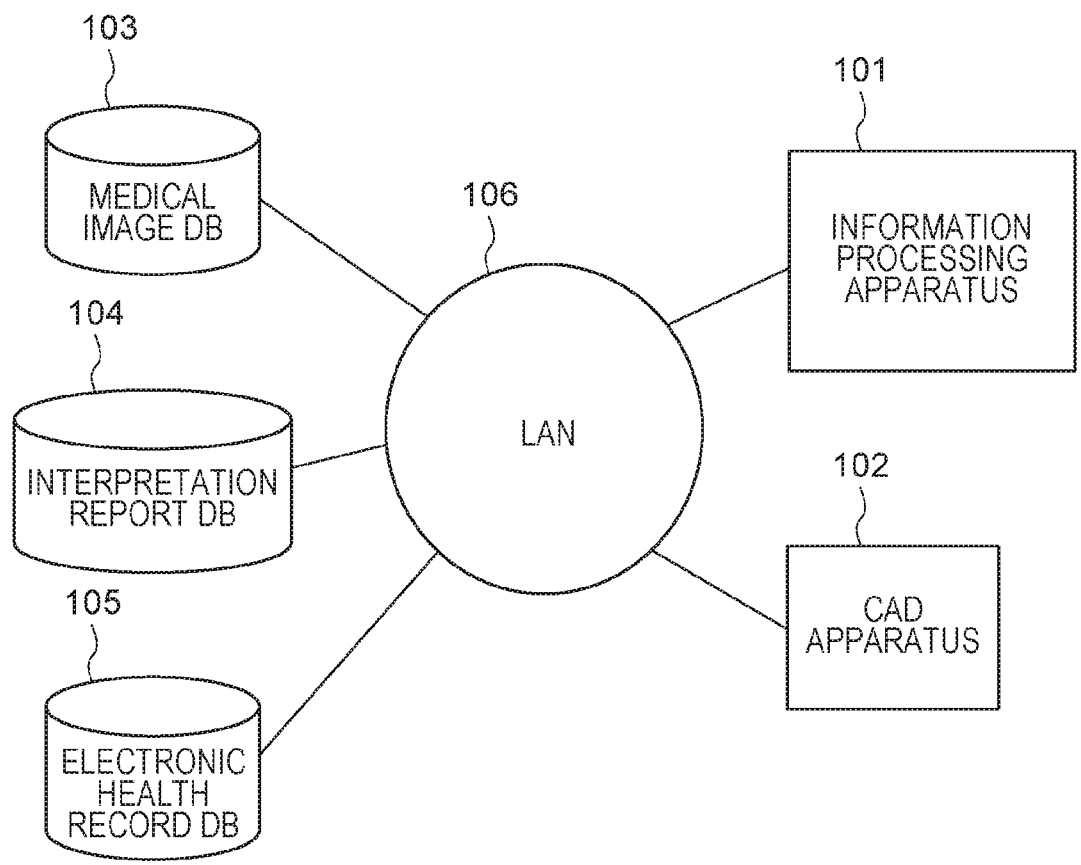
FIG. 1 is a diagram that shows an example of the configuration of a system including an information processing apparatus according to embodiments of the present invention.

FIG. 1 is a diagram that shows an example of the configuration of an information processing system including the information processing apparatus according to the first embodiment. The information processing system includes the information processing apparatus 101, the CAD apparatus 102, a medical image database (hereinafter, database is simply referred to as DB) 103, an interpretation report DB 104, an electronic health record DB 105, and a local area network (LAN) 106.

The information processing apparatus 101 acquires training data for machine training that is performed in the CAD apparatus 102 based on information acquired from the medical image DB 103, the interpretation report DB 104, and the electronic health record DB 105. The information processing apparatus 101 is, for example, a computer. Training data is a set of an input value and correct output value of an inferencer that performs machine training in the CAD apparatus 102. An example of training data will be described with reference to FIG. 4E.

The CAD apparatus 102 infers a disease associated with a new case through machine training using training data acquired by the information processing apparatus 101. The CAD apparatus 102 is, for example, a computer. The CAD apparatus 102, for example, infers a disease name based on a medical image and provides a doctor with information to aid the doctor in making a diagnosis. More specifically, the CAD apparatus 102, for example, acquires image findings by analyzing an input medical image and infers a disease name from the image findings with the use of the inferencer that has been trained on the relationship between image findings and a disease name. In the first embodiment, the following case will be described as an example. Based on image findings obtained by analyzing a lung nodule that a doctor has designated on a medical image, the inferencer infers the probability of each of the fact that the designated lung nodule is due to a lung cancer (original cancer), the fact that the designated lung nodule is due to a metastatic cancer, and the fact that the designated lung nodule is due to a benign nodule. The CAD apparatus 102 may provide a doctor with both image findings that are a basis for inference and the result of inference together.

The medical image DB 103 acquires medical images captured by various image capturing devices, such as a CT apparatus, via the LAN 106 from the image capturing devices and saves the medical images. The medical image DB 103 also provides the function to retrieve and acquire the saved medical information. A medical image is, for example, an image in the format of digital imaging and communications in medicine (DICOM). The medical image DB 103 is, for example, a picture archiving and communication system (PACS).

The interpretation report DB 104 acquires interpretation report information via the LAN 106 from a client device (not shown) that a doctor uses and saves the interpretation report information. The interpretation report DB 104 provides the function to retrieve and acquire the saved interpretation report information. Interpretation report information is, for example, a report describing image findings obtained by a doctor through observation of a medical image and information about a disease derived by a doctor from the image findings. An example of interpretation report information will be described later with reference to FIG. 4B.

The electronic health record DB 105 acquires electronic health record information via the LAN 106 from a client device (not shown) that a doctor uses and saves the electronic health record information. The electronic health record DB 105 also provides the function to retrieve and acquire the saved electronic health record information. Electronic health record information is, for example, a consultation record describing information obtained through interview or examination when a doctor has a consultation with a patient. An example of electronic health record information will be described later with reference to FIG. 4C.

The example in which the CAD apparatus 102 and the information processing apparatus 101 that acquires training data to be used in the CAD apparatus 102 are separate apparatuses is described; however, the present invention is not limited thereto. For example, the CAD apparatus 102 and the information processing apparatus 101 may be implemented by one and the same apparatus, or may be implemented by a system made up of a plurality of apparatuses for implementing the functions of the CAD apparatus 102 and the functions of the information processing apparatus 101.

Hardware Configuration

Figure 2:
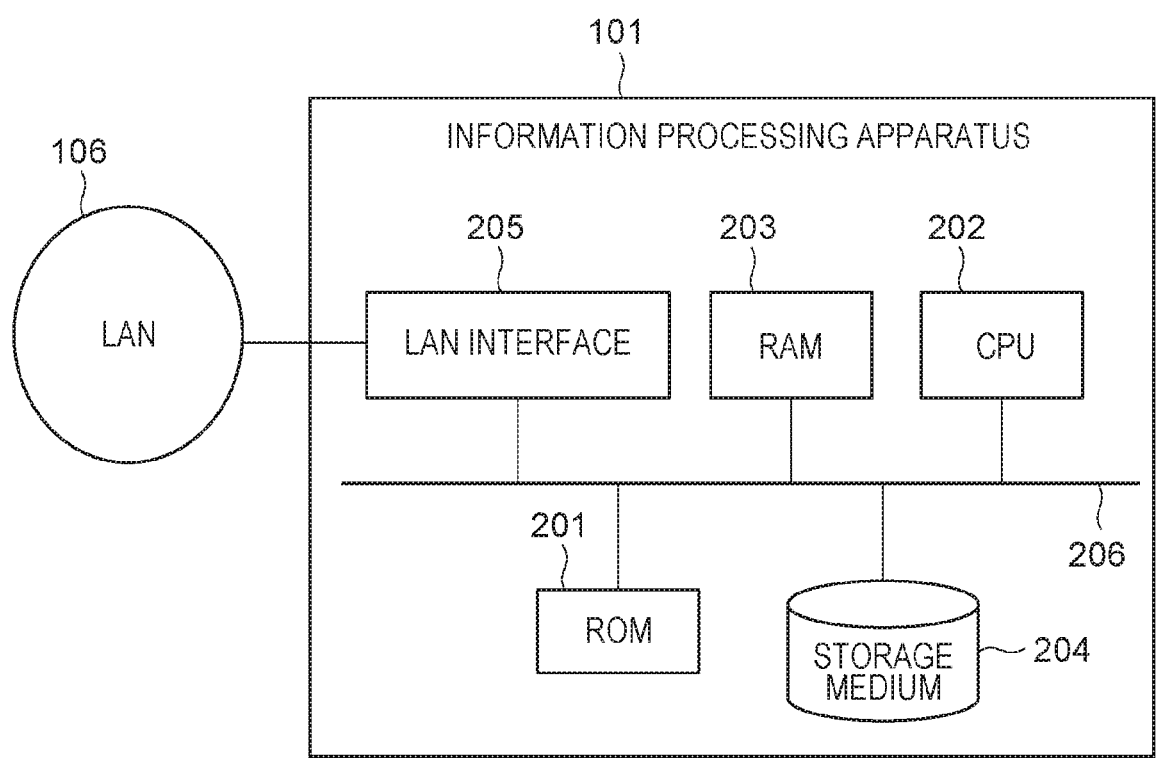
FIG. 2 is a diagram that shows an example of the hardware configuration of the information processing apparatus according to the embodiments of the present invention.

FIG. 2 is a diagram that shows an example of the hardware configuration of the information processing apparatus 101 according to the first embodiment. The information processing apparatus 101 includes a read only memory (ROM) 201, a central processing unit (CPU) 202, a random access memory (RAM) 203, a storage medium 204, a LAN interface 205, and a bus 206.

The ROM 201 stores a program, such as a basic input output system (BIOS), for initializing hardware and starting up an OS.

The CPU 202 executes arithmetic processing at the time of running the BIOS, the OS, or a processing program.

The RAM 203 temporarily stores information at the time when the CPU 202 runs a program.

The storage medium 204 stores programs and information for running the operating system (OS) and a process according to the first embodiment. The storage medium 204 is, for example, a hard disk drive (HDD) or a solid state drive (SSD).

The LAN interface 205 is an interface that supports standards, such as Institute of Electrical and Electronics Engineers (IEEE) 802.3ab, and that is used to carry out communication via the LAN 106.

The bus 206 is an internal bus in the information processing apparatus 101.

The information processing apparatus 101 may further include a GPU. Particularly, when the functions of the information processing apparatus 101 and the functions of the CAD apparatus 102 are implemented as one apparatus or one system, the GPU may make an inference.

The CPU 202 and the GPU each are an example of a processor. The ROM 201, the RAM 203, and the storage medium 204 each are an example of a memory. The information processing apparatus 101 may include a plurality of processors. In the first embodiment, the functions of the information processing apparatus 101 are implemented when the processor of the information processing apparatus 101 runs the programs stored in the memory. The information processing apparatus 101 may include a CPU, a GPU, or an application specific integrated circuit (ASIC), which exclusively executes a specific process. The information processing apparatus 101 may include a field-programmable gate array (FPGA) in which a specific process or all the processes are programmed. The information processing apparatus 101 may include a plurality of components as the storage medium 204. The information processing apparatus 101 may include a plurality of components for communication, such as the LAN interface 205.

The information processing apparatus 101 may be connected to an operating unit (not shown) for a user to input information to the information processing apparatus 101 and a display unit (not shown) for the information processing apparatus 101 to provide information to the user. The operating unit (not shown) is, for example, a keyboard, a mouse, or the like. The display unit (not shown) displays information based on control from the information processing apparatus 101. The display unit (not shown) provides an interface for receiving an instruction of a user based on control from the information processing apparatus 101. The display unit (not shown) is, for example, a liquid crystal display.

The operating unit (not shown) and the display unit (not shown) may be integrated as a touch panel display.

Functional Configuration

Figure 3:
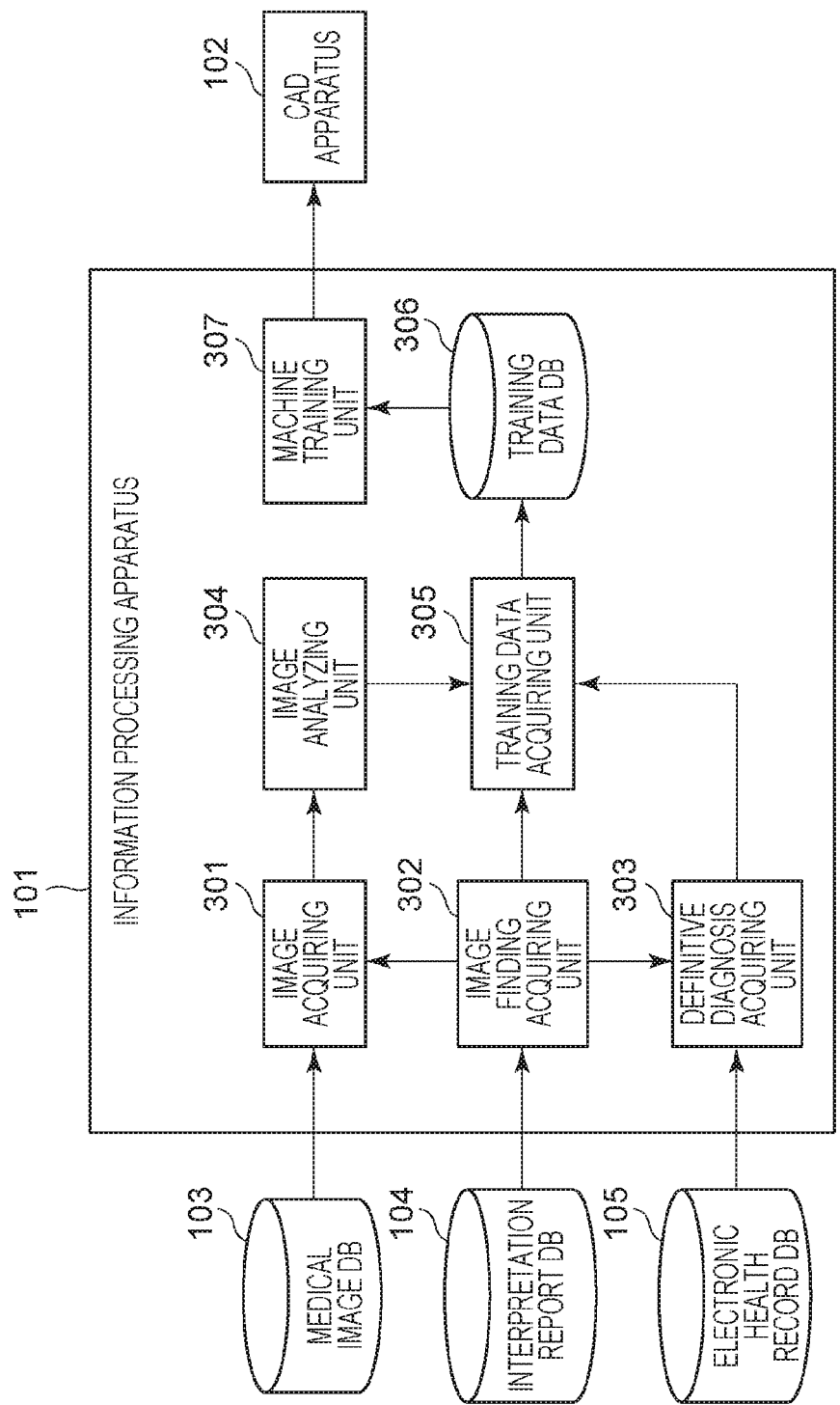
FIG. 3 is a diagram that shows an example of the functional configuration of the information processing apparatus according to the embodiments of the present invention.

FIG. 3 is a diagram that shows an example of the functional configuration of the information processing apparatus 101 according to the first embodiment. The information processing apparatus 101 is made up of an image acquiring unit 301, an image finding acquiring unit 302, a definitive diagnosis acquiring unit 303, an image analyzing unit 304, a training data acquiring unit 305, a training data DB 306, and a machine training unit 307.

The image acquiring unit 301 acquires a medical image from the medical image DB 103. The image acquiring unit 301 may acquire a medical image that a user designates or may acquire a medical image that is determined based on an interpretation report acquired by the image finding acquiring unit 302 (described later) or information contained in an electronic health record. A medical image that is identified based on information contained in an interpretation report or an electronic health record is, for example, medical information attached to the interpretation report or the electronic health record, or medical information captured in an examination associated with an examination ID contained in the interpretation report or the electronic health record. More specifically, based on an examination ID 423 of an interpretation report illustrated in FIG. 4B, the image acquiring unit 301 retrieves medical image information 411-$i$ (i=1, 2, . . . ) of the examination associated with the examination ID 423 from the medical image DB 103 and acquires the medical image information 411-$i$.

The image finding acquiring unit 302 acquires diagnosed information related to a case to be inferred. The following case will be described as an example. The image finding acquiring unit 302 acquires information contained in an interpretation report or an electronic health record and acquires information on image findings diagnosed for the case. For example, based on the details of text 425 of the interpretation report illustrated in FIG. 4B, the image finding acquiring unit 302 retrieves an interpretation report 421-$i$ (i=1, 2, . . . ) of a case, which is related to a lung nodule and which is to be inferred, from the interpretation report DB 104. The image finding acquiring unit 302 extracts information including image findings, an area, a patient ID, and an examination ID from the acquired interpretation report information 421-$i$. When information such as a representative image related to the case and the position of a lesion in an image is held in an interpretation report or an electronic health record, the image finding acquiring unit 302 extracts such information. Hereinafter, image findings acquired by the image finding acquiring unit 302 are referred to as first image findings. A first image finding is an example of first information. The image finding acquiring unit 302 is an example of a first acquiring unit.

The definitive diagnosis acquiring unit 303 acquires information about a definitive diagnosis that indicates a definitive disease name in relation to a diagnosed case of a patient. The definitive diagnosis acquiring unit 303, for example, retrieves electronic health record information 431-$i$ (i=1, 2, . . . ) of a patient associated with a patient ID 422 in the interpretation report information 421-$i$ acquired by the image finding acquiring unit 302 from the electronic health record DB 105, and acquires the electronic health record information 431-$i$. The definitive diagnosis acquiring unit 303 extracts a definitive diagnosis 437 from the electronic health record information 431-$i$.

The image analyzing unit 304 acquires image findings representing a feature visualized in a medical image acquired by the image acquiring unit 301 by analyzing the medical image.

Particularly, the image analyzing unit 304 acquires image findings representing the feature of a disease, visualized in the medical image. FIG. 4D illustrates an example of the information acquired by the image analyzing unit 304.

Hereinafter, image findings acquired by the image analyzing unit 304 are referred to as second image findings. A second image finding is an example of second information. The image analyzing unit 304 is an example of a second acquiring unit.

The training data acquiring unit 305 acquires training data to be used in machine training that the CAD apparatus 102 performs. The training data acquiring unit 305 acquires training data 451-$i$ (i=1, 2, . . . ) based on first image findings acquired by the image finding acquiring unit 302 and second image findings acquired by the image analyzing unit 304. The training data acquiring unit 305 further acquires training data 451-$i$ based on a definitive diagnosis acquired by the definitive diagnosis acquiring unit 303. The training data acquiring unit 305 saves the acquired training data 451-$i$ in the training data DB 306. The training data acquiring unit 305 is an example of a third acquiring unit that acquires training data for machine training.

The training data DB 306 saves training data 451-*i* acquired by the training data acquiring unit 305. The training data DB 306 also provides the functions to retrieve and acquire the saved training data. The training data DB 306 may be contained in the CAD apparatus 102 or may be implemented as an external DB connected to the information processing apparatus 101 and the CAD apparatus 102.

The machine training unit 307 performs machine training on the inferencer that the CAD apparatus 102 uses by using the training data 451-*i* of the training data DB 306. The machine training unit 307 may be included in the CAD apparatus 102 or may be included in the training data DB 306.

Configuration of Information

FIG. 4A to FIG. 4E are views that respectively show examples of the configurations of pieces of information that are acquired by the information processing apparatus 101.

Figure 4A:
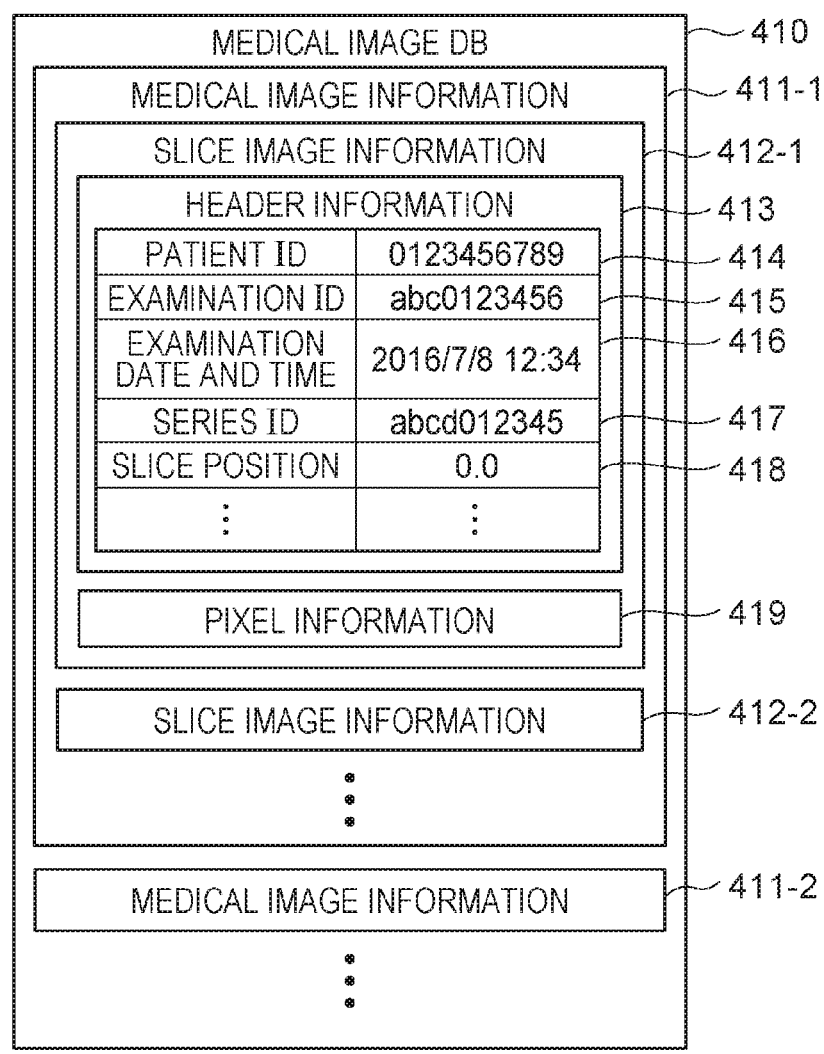
FIG. 4A is a view that shows an example of the configuration of information that is acquired by the information processing apparatus according to the embodiments of the present invention.

FIG. 4A is a view that shows an example of the configuration of information 410 that is saved in the medical image DB. The information 410 is composed of one or more pieces of medical image information 411-1, 411-2, . . . Medical image information 411-*i* (i=1, 2, . . . ) is, for example, image information that is obtained through exposure once, and, when a medical image is a three-dimensional image, the medical image is composed of one or more pieces of slice image information 412-1, 412-2, . . . Each piece of slice image information 412-*i* (i=1, 2, . . . ) is image information of one cross section and is composed of header information 413 and pixel information 419.

The header information 413 contains information such as a patient ID 414, an examination ID 415, an examination date and time 416, a series ID 417, and a slice position 418. A patient ID 414 is information that uniquely identifies a patient. An examination ID 415 is information that uniquely identifies an examination. An examination date and time 416 is a date and time at which an examination is carried out. A series ID 417 is information that uniquely identifies medical image information 411-*i* (i=1, 2, . . . ). A slice position 418 is a position of a cross section and is a relative distance in a body axis direction from a predetermined reference point. When a medical image is a three-dimensional image and is composed of a plurality of pieces of slice image information 412-*i*, the header information that is common among the slice images may be included in, for example, only the slice image information 412-1. Pixel information 419 is composed of, for example, 512×512 pixel values, and each pixel value is represented in 12-bit gray scale (one channel).

Figure 4B:
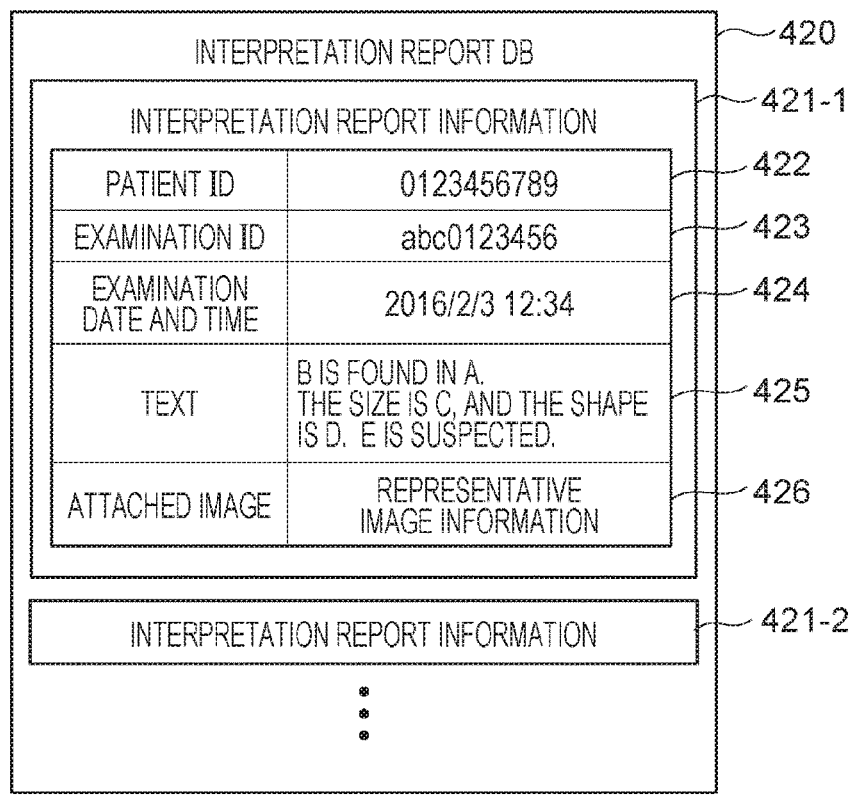
FIG. 4B is a view that shows an example of the configuration of information that is acquired by the information processing apparatus according to the embodiments of the present invention.

FIG. 4B is a view that shows an example of the configuration of information 420 that is saved in the Interpretation report DB 104. The information 420 is composed of one or more pieces of Interpretation report information 421-1, 421-2, . . . Interpretation report information 421-*i* (i=1, 2, . . . ) contains pieces of information, that is, a patient ID 422, an examination ID 423, an examination date and time 424, text 425, and an attached image 426. Text 425 contains the details of diagnostic imaging in, for example, natural sentence, and reads in the example of FIG. 4B that "B is found in A. The size is C, and the shape is D. E is suspected." Here, "A" is a word representing an area, "B" is a word representing a lesion, "C" and "D" are words representing an image finding, and "E" is a word representing the result of diagnostic imaging. A word means a character or character string in a sentence, and is a unit that represents a meaning in a sentence. An attached image 426 is, for example, information related to a medical image that a doctor who writes an interpretation report attaches to the interpretation report as a representative image considered to represent the details in text 425. An attached image 426 is, for example, information of an image converted from the pixel information 419 of slice image information 412-*i* (i=1, 2, . . . ) into 8-bit bitmap format, or the like. An attached image 426 may be link information to slice image information 412-*i* (i=1, 2, . . . ) or other converted image information in bitmap format, or the like. The information 420 may contain information (not shown) that summarizes the details of text 425 and that is called "impression". The information 420 may contain information that indicates the position or region of a lesion in an interpreted medical image in at least any one of text 425 and other information (not shown).

Figure 4C:
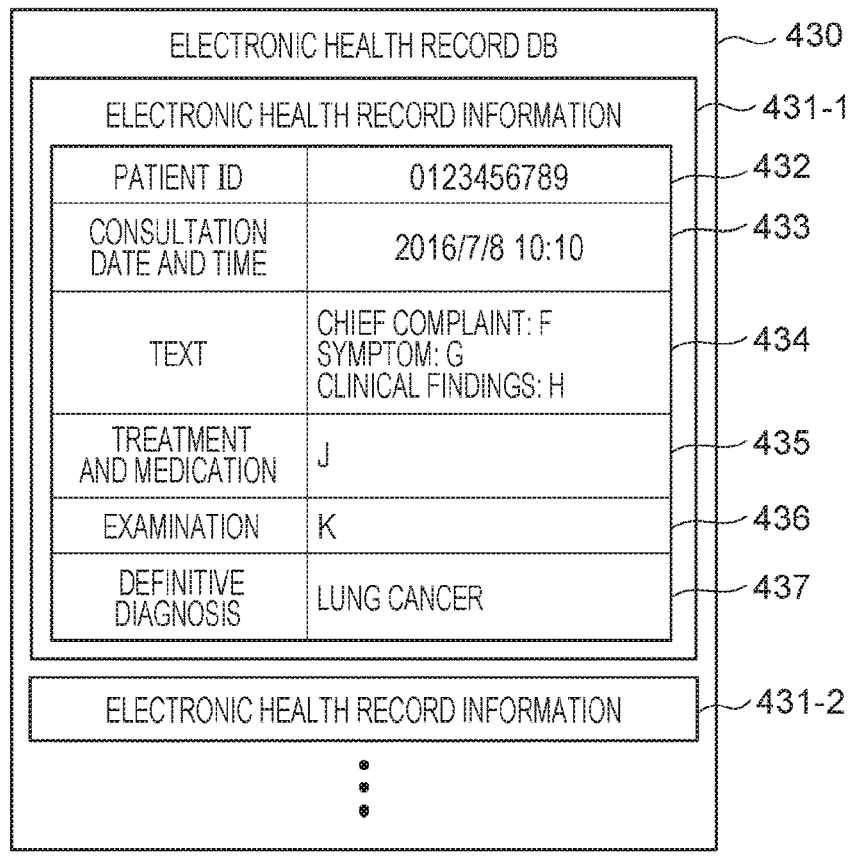
FIG. 4C is a view that shows an example of the configuration of information that is acquired by the information processing apparatus according to the embodiments of the present invention.
Figure 4D:
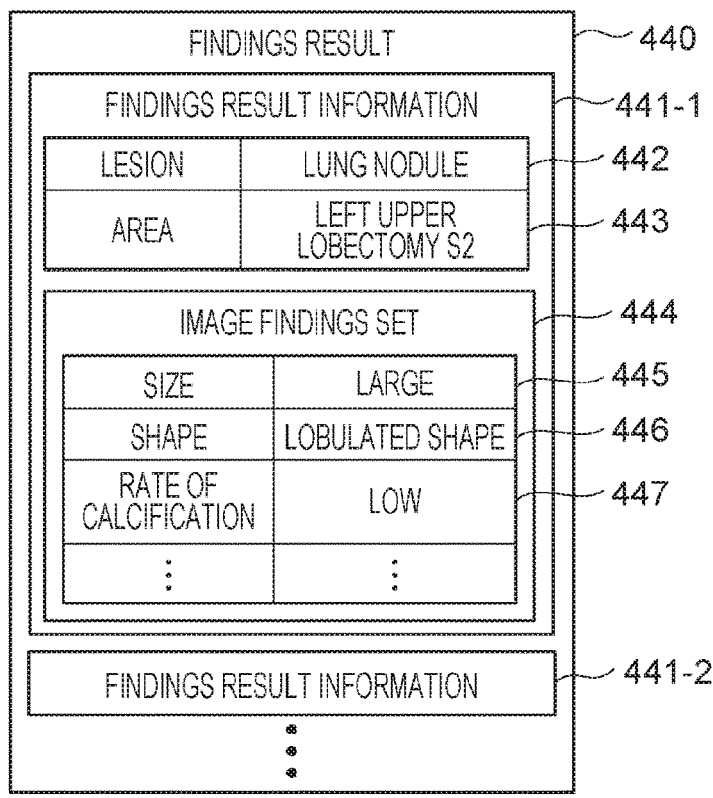
FIG. 4D is a view that shows an example of the configuration of information that is acquired by the information processing apparatus according to the embodiments of the present invention.

FIG. 4C is a view that shows an example of the configuration of information 430 that is saved in the electronic health record DB 105. The information 430 is composed of one or more pieces of electronic health record information 431-1, 431-2, . . . Electronic health record information 431-*i* (i=1, 2, . . . ) contains pieces of information, that is, a patient ID 432, a consultation date and time 433, text 434, treatment and medication 435, an examination 436, and a definitive diagnosis 437.

The consultation date and time 433 indicates a date and time at which consultation is performed. The text 434 shows the details of consultation. The treatment and medication 435 shows the details of treatment action and medication. The examination 436 indicates the details of examinations, such as diagnostic imaging, blood test, and pathology test. The definitive diagnosis 437 is information that indicates a disease name finally diagnosed by a doctor based on the result of pathology test, or the like.

FIG. 4D is a view that shows an example of the configuration of information 440 that contains second image findings acquired by the image analyzing unit 304. The information 440 is composed of findings result information 441-1, 441-2, . . . , each of which the image analyzing unit 304 generates for a case for training. Findings result information 441-*i* (i=1, 2, . . . ) contains pieces of information, that is, a lesion 442, an area 443, and an image findings set 444. The image findings set 444 is composed of one or more image findings. Each of the image findings is composed of an item of an image finding (hereinafter, referred to as image finding item or finding item) and the value of the item. Examples of the image finding item include size 445, shape 446, and rate of calcification 447. The size 445 is an item that indicates, for example, the longitudinal diameter of a lung nodule, and takes, for example, a three-level value, that is, "large", "middle", or "small". The shape 446 is an item that indicates, for example, the shape of the lung nodule, and takes, for example, a state, that is, "spherical", "subspherical shape", "lobulated shape", or the like, as a value. The rate of calcification 447 is an item that indicates, for example, the percentage of pixels having a pixel value corresponding to calcification among pixels in a lung nodule, and takes, for example, a four-level value, that is, "high", "middle", "low", or "none". The value of each finding item may be a numeric value. The numeric value may be a continuous value or a discrete value or a range. The type or value of each image finding item is not limited to the above-described examples.

Figure 4E:
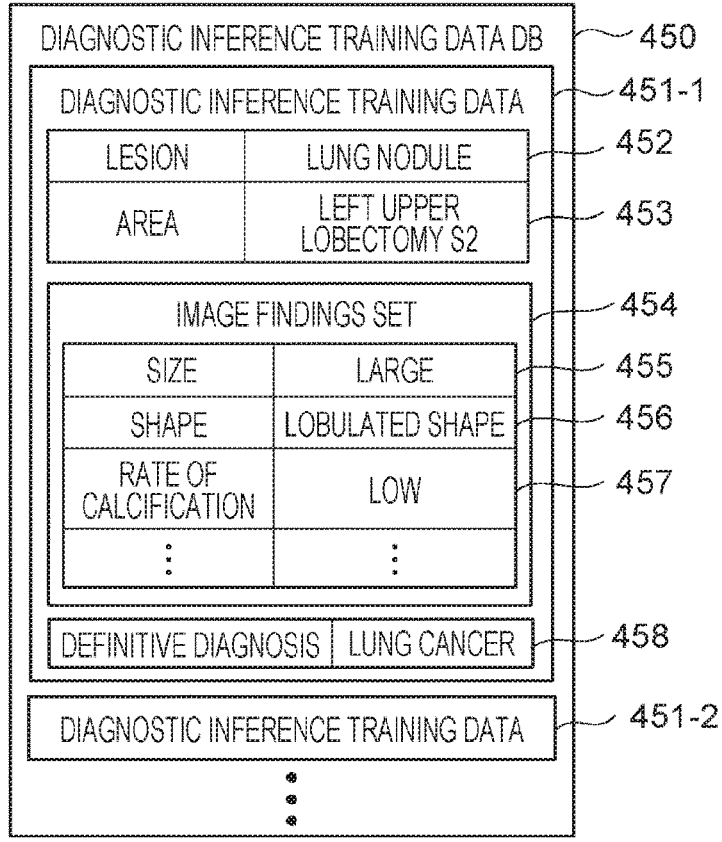
FIG. 4E is a view that shows an example of the configuration of information that is acquired by the information processing apparatus according to the embodiments of the present invention.

FIG. 4E is a view that shows an example of the configuration of information 450 that is saved in the training data DB 306. The information 450 that is saved in the training data DB 306 is composed of one or more pieces of training data 451-1, 451-2, . . . Training data 451-*i* (i=1, 2, . . . ) contains pieces of information, that is, a lesion 452, an area 453, an image findings set 454, and a definitive diagnosis 458. It is assumed that the image findings set 454 has a similar configuration to that of the above-described image findings set 444.

Series of Processing

FIG. 5 is a flowchart that shows an example of a process that is executed by the information processing apparatus 101 according to the first embodiment. Hereinafter, an example of the process in which first image findings are acquired based on information acquired from the interpretation report DB 104, a definitive diagnosis is acquired based on information acquired from the electronic health record DB 105, second image findings are acquired by analyzing a medical image acquired from the medical image DB 103, and training data is acquired based on the first image findings and the second image findings will be described.

In step S501, the image finding acquiring unit 302 acquires a case(s) related to a target to be inferred from among cases saved in the interpretation report DB 104 and acquires its/their image findings, that is, first image findings. For example, when a diagnosis of a lung nodule is inferred in the CAD apparatus 102, an interpretation report having a diagnosis of a lung nodule is retrieved and acquired from the interpretation report DB 104 as a candidate for training data that is used in machine training for the inference. Specifically, the image finding acquiring unit 302 retrieves an interpretation report containing a keyword "lung nodule" in the text of interpretation report information from the interpretation report DB 104. The image finding acquiring unit 302 acquires first image findings of the intended case by applying a process called morphological analysis and syntactic analysis to the text 425 of Interpretation report information 421-$i$ ($i$=1, 2, . . . ).

In some of finding items, nothing contained in an interpretation report implicitly means that there is no image finding associated with the finding item. Such a finding item may be defined in advance, and, when nothing can be acquired from the report in association with the finding item, the image finding acquiring unit 302 may acquire the value "none" in association with the finding item.

In step S502, the definitive diagnosis acquiring unit 303 acquires information that indicates a finally diagnosed disease name for each of the cases acquired in step S501. The definitive diagnosis acquiring unit 303 retrieves information about the intended case from the electronic health record DB 105 and acquires a definitive diagnosis 437. For example, the definitive diagnosis acquiring unit 303 retrieves electronic health record information 431-$i$ ($i$=1, 2, . . . ) of a patient based on the value of the patient ID 422 of the interpretation report information 421-$i$ acquired in step S501. The definitive diagnosis acquiring unit 303 acquires the definitive diagnosis 437 of the intended case by reading a predetermined field of the electronic health record information 431-$i$. Alternatively, the definitive diagnosis acquiring unit 303 may acquire a disease name of the case by applying a process called morphological analysis or syntactic analysis to information contained in the electronic health record information 431-$i$.

In step 503, the image acquiring unit 301 acquires medical image information 411-$i$ ($i$=1, 2, . . . ) associated with each of the cases acquired in step S501 from the medical image DB 103.

For example, the image acquiring unit 301 retrieves the medical image information 411-$i$ of the intended case based on the value of the examination ID 423 contained in the interpretation report information 421-$i$ acquired in step S501 from the medical image DB 103.

With the above-described process of step S501 to step S503, the information processing apparatus 101 acquires medical images of cases, first image findings on some finding items, and definitive diagnoses that are pieces of information about finally diagnosed disease names, from existing diagnosed data of patients.

In step S504, the image analyzing unit 304 acquires image findings through image analysis, that is, second image findings, from the medical image information 411-$i$ acquired in step S503. Specifically, the image analyzing unit 304 determines the position of a lesion on an image, contained in an interpretation report, in the following procedure. When the interpretation report information 421-$i$ holds information that indicates the position of a lesion, the image analyzing unit 304 sets the value to the position of the lesion in a medical image. When the interpretation report information 421-$i$ holds information about a representative image, the image analyzing unit 304 searches a three-dimensional image for an image similar to the representative image and determines the slice position of a slice image having a high similarity to the representative image. The image analyzing unit 304 executes a process of detecting a lung nodule over the determined slice image and detects the position of a lesion on the slice image. When the interpretation report information 421-$i$ does not hold information that indicates the position of a lesion and does not hold information of a representative image, the image analyzing unit 304 executes a process of detecting a lung nodule over all the slice images of the three-dimensional image or a slice image that is determined based on the other information contained in the interpretation report information 421-$i$ and detects the position of a lesion.

When the position of a lesion is detected, the image analyzing unit 304 acquires second image findings by applying an image analyzing process over a three-dimensional image near the position of the lesion. For example, the image analyzing unit 304 acquires image findings by using convolutional neural network (CNN) that has been subjected to machine training in advance on the relationship between the three-dimensional image of the lesion and individual image findings. The finding items of second image findings that the image analyzing unit 304 acquires need not be all the finding items in a diagnosis of a lung nodule. For example, finding items that can be acquired with a reliability (correct answer rate) higher than or equal to a certain degree through image analysis may be defined in advance, and the image analyzing unit 304 may acquire second image findings only in association with those finding items.

In step S505, the training data acquiring unit 305 acquires training data 451-$i$ based on the first image findings acquired in step S501 and the second image findings acquired in step S504. The training data acquiring unit 305 further acquires training data 451-$i$ based on the definitive diagnosis acquired in step S502. The training data acquiring unit 305 saves the training data 451-$i$ in the training data DB 306. The details of a process of acquiring training data in step S505 will be described later with reference to FIG. 6.

In step S506, the machine training unit 307 performs machine training on the inferencer that is used in the CAD apparatus 102 by using the training data 451-$i$ saved in the training data DB 306. In the example described in the first embodiment, the machine training unit 307 adjusts parameters of the inferencer such that the rate of coincidence between the disease name that is the inferred result when image findings that are input data are input to the inferencer and the definitive diagnosis (disease name) that is the correct answer data is maximal.

Figure 6:
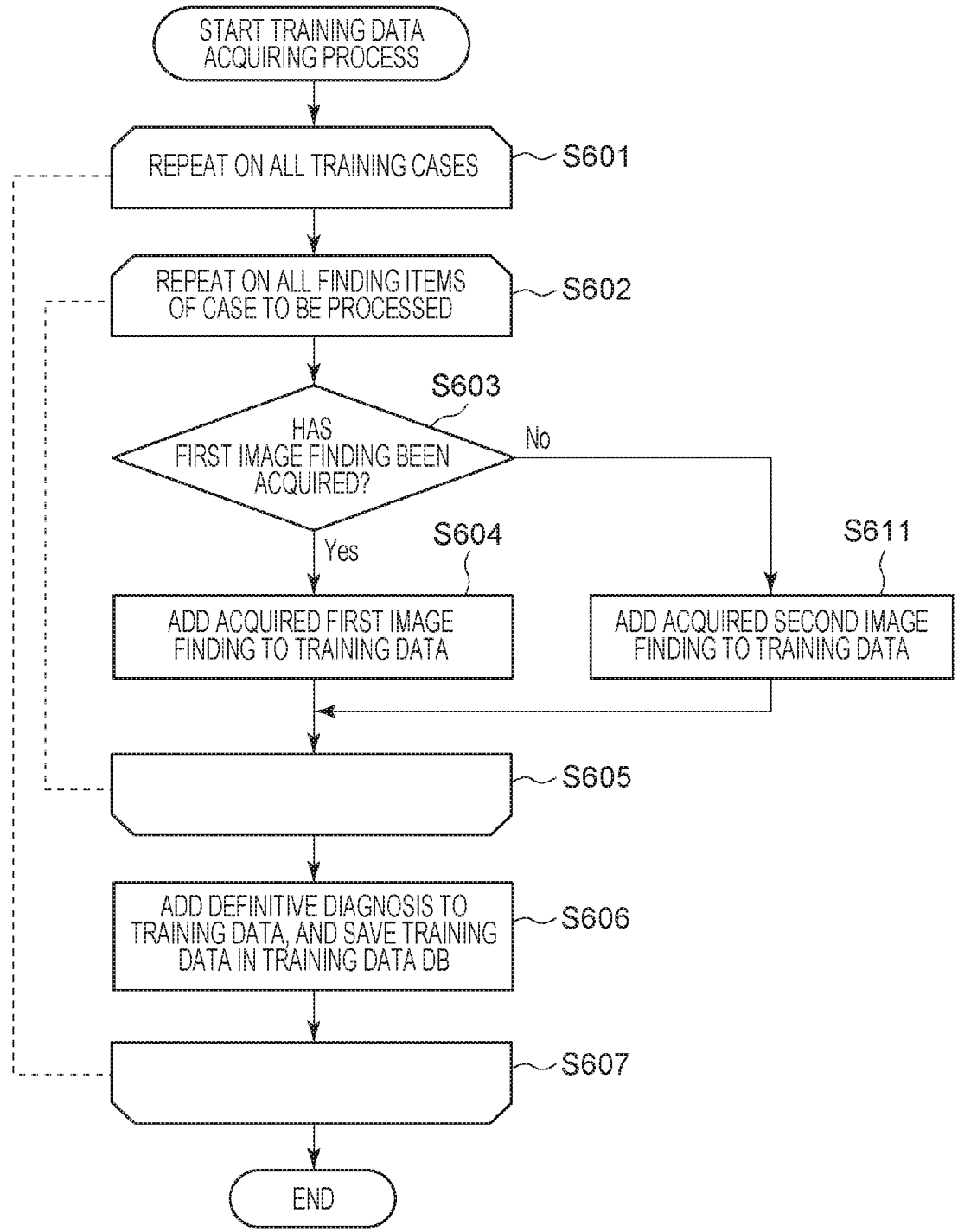
FIG. 6 is a flowchart that shows an example of a process that is executed by the information processing apparatus according to the first embodiment.

FIG. 6 is a flowchart that shows an example of a process of acquiring training data, which the training data acquiring unit 305 executes in step S505. As the process of acquiring training data is started, the process of step S601 to step S607 is repeated. In the repeated process, the process of step S602 to step S605 is repeated on each of the image finding items of the intended i-th (i=1, 2, . . . ) case.

Step S601 to step S607, and step S611 make up a process that is executed on each of at least one case that is a candidate for training data, and make up a repeated process that is executed over all the cases acquired in step S501.

Step S602 to step S605, and step S611 make up a process that is executed on each of at least one finding item included in the i-th case and make up a repeated process that is executed over all the at least one finding item.

In step S603, the training data acquiring unit 305 determines whether the first image findings of the i-th case have been acquired in step S501. When the first image findings have been acquired, the process proceeds to step S604; otherwise, the process proceeds to step S611.

In step S604, the training data acquiring unit 305 adds the first image findings acquired in step S501 to the image findings set 454 of the training data 451-*i*.

In step S611, the training data acquiring unit 305 adds the second image findings acquired in step S504 to the image findings set 454 of the training data 451-*i*. In the loop of step S602 to step S605, when the intended finding item is not the finding item of which a second image finding is not acquired, the process of step S611 is skipped.

When the repeated process of step S602 to step S605, and step S611 completes for all the finding items, the process proceeds to step S606.

In the process of step S606, the training data acquiring unit 305 adds the definitive diagnosis acquired in step S502 to the definitive diagnosis 458 of the training data 451-*i*.

When the repeated process of step S601 to step S607, and step S611 completes for all the cases, the process shown in FIG. 6 ends.

With the information processing apparatus 101 according to the first embodiment, training data can be acquired based on first image findings and second image findings. Particularly, when some of first image findings input in existing data are lacking, second image findings acquired through image analysis are used to compensate for the lacking data. Training data is acquired based on first image findings and second image findings, and the training data is used for machine training. Thus, the accuracy of inference that is made by the CAD apparatus 102 is improved. Particularly, when some of first image findings are lacking, a decrease in the accuracy of inference that is made by the CAD apparatus 102 for the lacking data is prevented.

First Modification of First Embodiment

The method of acquiring existing data that is used as a candidate for training data is not limited to the above-described example. For example, as long as a medical image of a case, first image findings on some finding items, and a finally diagnosed disease name (definitive diagnosis) are acquired with a method, these pieces of information may be acquired from one data, or these pieces of information may be acquired from a plurality of associated pieces of information, or these pieces of information may be acquired with any method.

For example, the case where the image finding acquiring unit 302 acquires first image findings from interpretation report information is described as an example. Alternatively, the image finding acquiring unit 302 may acquire first image findings from electronic health record information, or may acquire first image findings by reading information from another case database (not shown), or may cause a display unit (not shown) to display an interface for a user to input first image findings, and may acquire information input by a user as first image findings.

When interpretation report information is structured, the image finding acquiring unit 302 may acquire selected information, such as image findings, from a predetermined field. A structured interpretation report is an interpretation report in which items to be contained as the interpretation report and their details are contained in a predetermined format and the items and the details of the items (that is, the values of the items) are explicitly associated with each other. Information that indicates the relevancy among the input items may be given to a structured interpretation report. A structured interpretation report may be configured such that the structure of an interpretation report or the relationship among pieces of information in the interpretation report may be expressed by codes defined in advance as in the case of a structured report (SR) that is regulated in digital imaging and communications in medicine (DICOM).

The definitive diagnosis acquiring unit 303 may acquire a definitive diagnosis that is a finally diagnosed disease name from other information attached to electronic health record information, such as a result of pathology test. When a definitive diagnosis is written in text in natural sentence, the definitive diagnosis acquiring unit 303 may acquire the definitive diagnosis with a morphological analysis technology, a syntactic analysis technology, and a medical dictionary. When there is a plurality of pieces of information about a disease name that a doctor diagnoses, the priority order of the information sources may be determined in advance. For example, the definitive diagnosis acquiring unit 303 may preferentially acquire a disease name diagnosed based on the result of pathology test as a definitive diagnosis. The definitive diagnosis acquiring unit 303 may determine a definitive diagnosis based on a change over time in information acquired from the details of an electronic health record and interpretation report. For example, the definitive diagnosis acquiring unit 303 may acquire a disease name determined in advance according to a degree to which the size of a lung nodule has changed in a predetermined period as a definitive diagnosis.

Second Modification of First Embodiment

A technique with which the image analyzing unit 304 acquires second image findings in step S504 is not limited to the above-described example. For example, the image analyzing unit 304 may acquire second image findings with a machine training technique, such as support vector machine (SVM) or random forest, based on an image feature vector.

The case where the image analyzing unit 304 acquires second image findings with a classifier on which machine training has been performed in advance is described as an example. Alternatively, the image analyzing unit 304 may acquire second image findings through rule-based processing based on an image feature vector. When an image feature vector convertible to image findings are designed in advance, the image analyzing unit 304 may acquire second image findings from an image feature vector based on the design. The image analyzing unit 304 may use a method appropriate for each of finding items of second image findings as a method of acquiring second image findings.

Third Modification of First Embodiment

The case where the image analyzing unit 304 acquires second image findings for all the image finding items that can be acquired through image analysis in step S504 is described as an example; however, the present invention is not limited thereto. For example, the image analyzing unit 304 does not need to acquire a second image finding for a finding item that hardly influences on machine training even when the value is lacking. The image analyzing unit 304 may acquire only second image findings associated with finding items of which first image findings have not been acquired in step S501.

Second Embodiment

In a second embodiment, as well as the first embodiment, the information processing apparatus 101 that acquires training data for the CAD apparatus 102 that infers a diagnosis of a lung nodule shadow will be described. The information processing apparatus 101 according to the second embodiment selects training data based on first image findings and second image findings. Particularly, when the details of the first image findings differ from the details of the second image findings, the information processing apparatus 101 determines that the case has a low degree of reliability as training data, and does not select the case as training data.

The system configuration including the information processing apparatus 101 according to the second embodiment, the hardware configuration and functional configuration of the information processing apparatus 101, the configuration of various pieces of information, which are acquired by the information processing apparatus 101, and the process that is executed by the information processing apparatus 101 are respectively similar to those of the first embodiment described with reference to FIG. 1, FIG. 2, FIG. 3, FIG. 4A to FIG. 4E, and FIG. 5, so the above description is incorporated herein, and the detailed description is omitted. Unless otherwise specified, like reference numerals denote the components described in the first embodiment.

Figure 7:
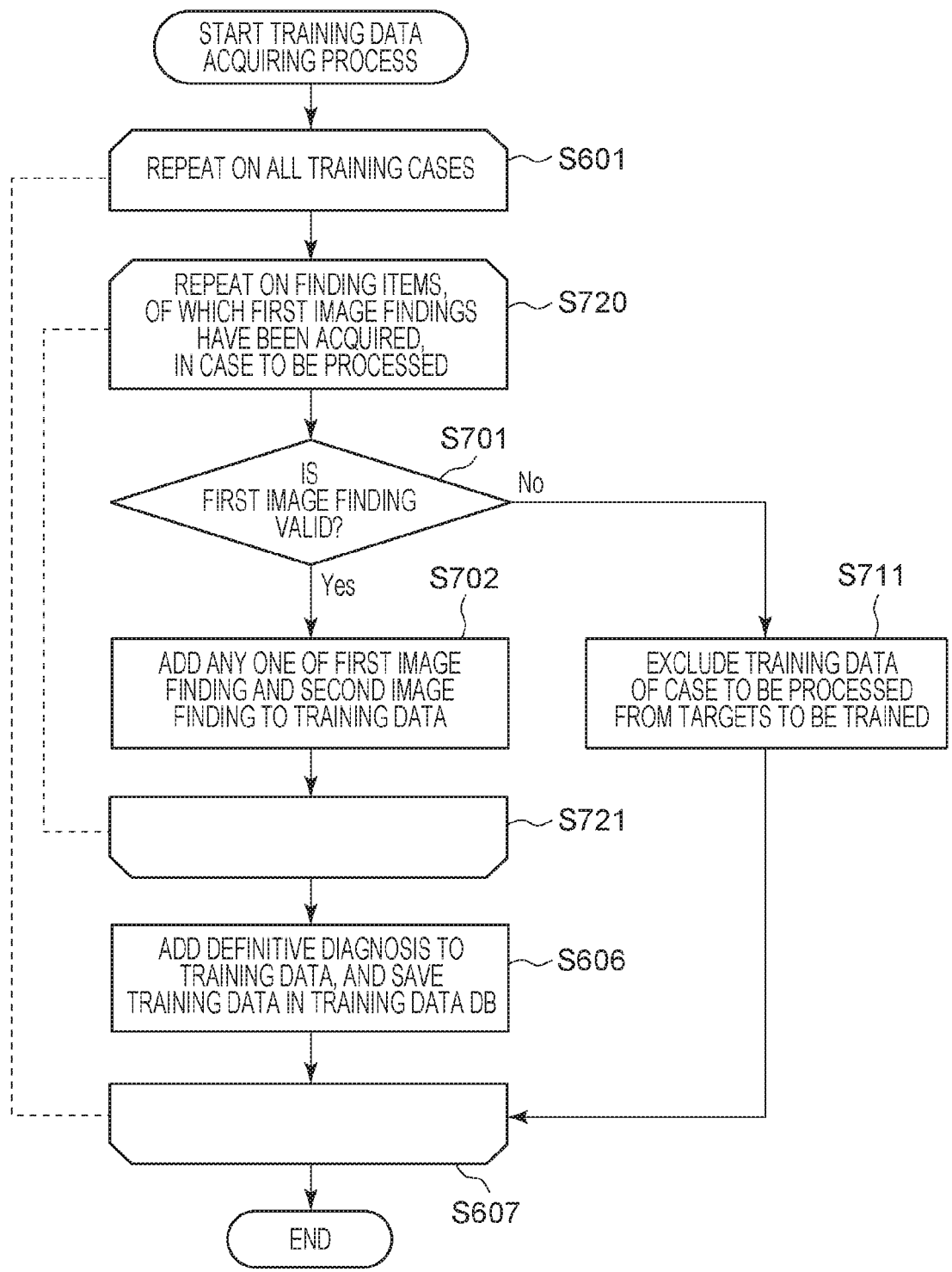
FIG. 7 is a flowchart that shows an example of a process that is executed by the information processing apparatus according to the second embodiment.

FIG. 7 is a flowchart that shows an example of a process that the training data acquiring unit 305 acquires training data in step S505 shown in FIG. 5.

Step S601, step S606, step S607, step S701, step S702, step S711, step S720 and step S721 make up a process that is executed on each of at least one case that is a candidate for training data, and make up a repeated process that is executed over all the cases acquired in step S501.

Step S701, step S702, step S711, step S720 and step S721 make up a process that is executed on each of the first image findings acquired for the i-th case, and make up a repeated process that is executed over all the finding items of the acquired first image findings.

In step S701, the training data acquiring unit 305 determines whether the first image findings are used as training data based on the first image findings acquired in step S501 and the second image findings acquired in step S504. Specifically, the training data acquiring unit 305 determines whether the first image findings are valid as training data based on a comparison between the first image findings and the second image findings. In terms of this point, the training data acquiring unit 305 is an example of a determining unit.

For example, when the degree of coincidence between the first image findings and the second image findings exceeds a predetermined reference, the training data acquiring unit 305 determines that the first image findings are used as training data. The degree of coincidence between two image findings is determined by using, for example, a thesaurus that defines synonyms, near-synonyms, and inclusion relation of image findings. The predetermined reference may be set for each finding item. For example, the predetermined reference may be set by a user in advance based on the degree of reliability of second image findings. For example, the reference of the degree of coincidence can be increased for a finding item of which the degree of reliability of second image findings is high, and the reference of the degree of coincidence can be decreased for a finding item of which the degree of reliability of second image findings is low. The degree of reliability of second image findings is evaluated based on, for example, a correct answer rate of second image findings obtained by analyzing a medical image of a case whose findings considered to be correct have been already known. For finding items of which second image findings are not acquired or finding items of which the degree of reliability of second image findings is lower than a predetermined value, determination in step S701 need not be carried out, and the process may proceed to step S702. When it is determined that first image findings are used as training data, the process proceeds to step S702; when it is determined that first image findings are not used as training data, the process proceeds to step S711.

In step S711, the training data acquiring unit 305 executes control such that the case to be processed in the loop is not used as training data to infer a diagnosis. Specifically, the training data acquiring unit 305 does not add the case to the training data 451-*i* (i=1, 2, . . . ).

In step S702, the training data acquiring unit 305 adds the first image findings acquired in step S501 to the image findings set 454 of the training data 451-*i*. For finding items of which the degree of reliability of second image findings is higher than or equal to the predetermined value, the training data acquiring unit 305 may add the second image findings to the training data instead of the first image findings.

In the second embodiment, the case where it is determined whether first image findings are used as training data based on the degree of coincidence between the first image findings and second image findings is described as an example. Alternatively, for example, the weight of training of the case is set according to the degree of coincidence, and first image findings and second image findings may be used as training data.

With the information processing apparatus 101 according to the second embodiment, information that is used as training data may be selectively acquired based on information contained in an interpretation report, an electronic health record, or the like, and information acquired by analyzing a medical image. Specifically, the information processing apparatus 101 may determine and select whether information about a certain case is used as training data based on the degree of coincidence between first image findings and second image findings. Thus, the information processing apparatus 101 is able to execute control such that, for example, a case whose interpretation report contains an error or another fault, a case whose information cannot be acquired from an interpretation report, or the like, is not used as training data. By determining whether information is used as training data, the accuracy of inference to be made by the CAD through machine training using the training data is improved.

Third Embodiment

In a third embodiment, as well as the first embodiment, the information processing apparatus 101 that acquires training data for the CAD apparatus 102 that infers a diagnosis of a lung nodule shadow will be described. The information processing apparatus 101 according to the third embodiment selects training data based on first image findings and second image findings. Particularly, when first image findings cannot be acquired from the databases, the information processing apparatus 101 uses second image findings acquired from a medical image of the intended case as training data.

The system configuration including the information processing apparatus 101 according to the third embodiment, the hardware configuration and functional configuration of the information processing apparatus 101, the configuration of various pieces of information, which are acquired by the information processing apparatus 101, and the process that is executed by the information processing apparatus 101 are respectively similar to those of the first embodiment described with reference to FIG. 1, FIG. 2, FIG. 3, FIG. 4A to FIG. 4E, and FIG. 5, so the above description is incorporated herein, and the detailed description is omitted. Unless otherwise specified, like reference numerals denote the components described in the first embodiment.

Figure 8:
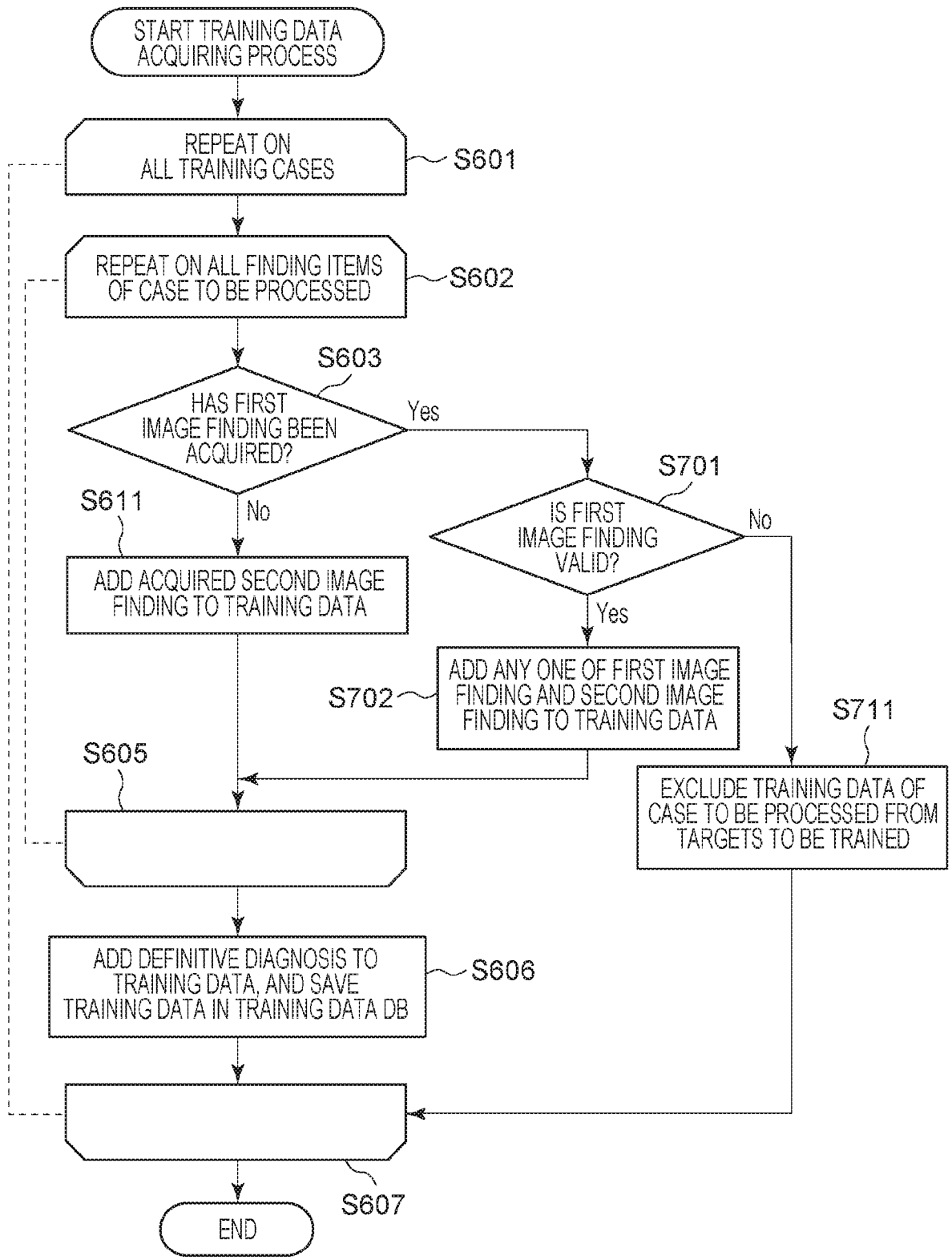
FIG. 8 is a flowchart that shows an example of a process that is executed by the information processing apparatus according to the third embodiment.

FIG. 8 is a flowchart that shows an example of a process that the training data acquiring unit 305 acquires training data in step S505 shown in FIG. 5.

Step S601, step S602, step S603, step S605, step S606, step S607, step S611, step S701, step S702 and step S711 make up a process that is executed on each of at least one case that is a candidate for training data, and make up a repeated process that is executed over all the cases acquired in step S501.

Step S602, step S603, step S605, step S611, step S701, step S702 and step S711 make up a process that is executed on each of the first image findings acquired for the i-th case, and make up a repeated process that is executed over all the finding items.

The training data acquiring unit 305 determines whether first image findings of the i-th case have been acquired (step S603). When the first image findings have not been acquired (No in step S603), the training data acquiring unit 305 uses second image findings acquired by analyzing a medical image of the case as training data (step S611). On the other hand, when the first image findings have been acquired (Yes in step S603), the training data acquiring unit 305 determines whether the first image findings are used as training data (step S701). When it is determined that the first image findings are used as training data, the first image findings or the second image findings are used as training data (step S702). When it is determined that the first image findings are not used as training data (No in step S701), the training data acquiring unit 305 does not use the i-th case as training data (step S711). When the i-th case is used as training data, the training data acquiring unit 305 adds a definitive diagnosis that is the diagnosed disease name of the case to training data and saves the definitive diagnosis in the training data DB 306 (step S606).

In the third embodiment, the case where it is determined whether first image findings are used as training data based on the first image findings and second image findings is described as an example. Alternatively, the weight of training of the case may be set according to a determined result, and first image findings and second image findings may be used for training.

With the information processing apparatus 101 according to the third embodiment, training data can be acquired based on first image findings and second image findings. Particularly, when some of first image findings input in existing data are lacking, second image findings acquired through image analysis are used to compensate for the lacking data. Information that is used as training data may be selectively acquired based on information contained in an interpretation report, an electronic health record, or the like, and information acquired by analyzing a medical image. Thus, the accuracy of inference to be made by the CAD through machine training using the training data acquired by the information processing apparatus 101 is improved.

Fourth Embodiment

In a fourth embodiment, as well as the first embodiment, the information processing apparatus 101 that acquires training data for the CAD apparatus 102 that infers a diagnosis of a lung nodule shadow will be described. When an image finding on a finding item has not been acquired from information, such as an interpretation report, the information processing apparatus 101 according to the fourth embodiment switches whether image findings acquired from an image of the case are used or the case is excluded from targets to be trained according to the degree of importance of the finding item.

The system configuration including the information processing apparatus 101 according to the fourth embodiment, the hardware configuration and functional configuration of the information processing apparatus 101, the configuration of various pieces of information, which are acquired by the information processing apparatus 101, and the process that is executed by the information processing apparatus 101 are respectively similar to those of the first embodiment described with reference to FIG. 1, FIG. 2, FIG. 3, FIG. 4A to FIG. 4E, and FIG. 5, so the above description is incorporated herein, and the detailed description is omitted. Unless otherwise specified, like reference numerals denote the components described in the first embodiment.

The training data acquiring unit 305 of the information processing apparatus 101 according to the fourth embodiment includes an importance acquiring unit (not shown). The importance acquiring unit (not shown) determines the degree of importance of a finding item based on information defined in advance for each finding item, such as a finding item importance definition information list 900 (hereinafter, referred to as information list 900) illustrated in FIG. 9.

Figure 9:
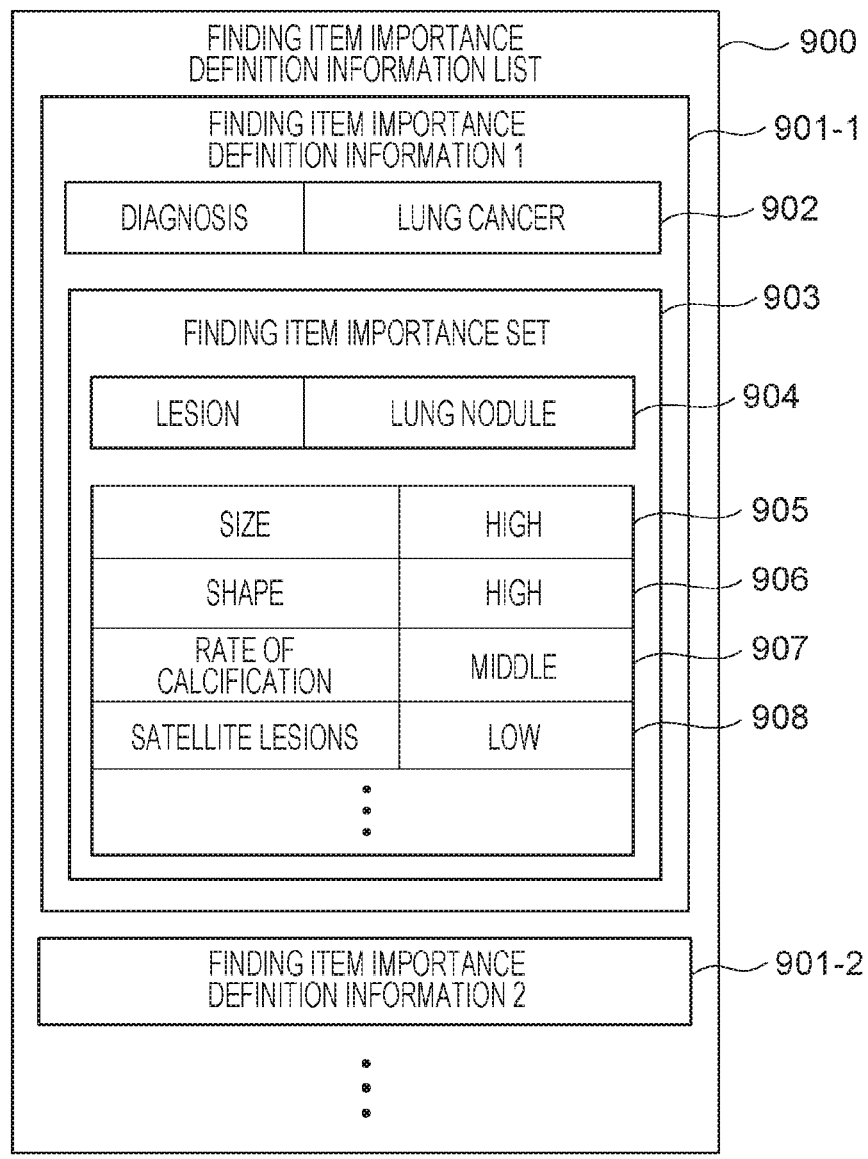
FIG. 9 is a view that shows an example of the configuration of information that is acquired by the information processing apparatus according to the fourth embodiment.

FIG. 9 is a view that shows an example of the configuration of the information list 900. The information list 900 includes one or more pieces of finding item importance definition information (hereinafter, referred to as definition information) 901-1, 901-2, . . . The definition information 901-$i$ ($i$=1, 2, . . . ) contains pieces of information, that is, a diagnosis 902 and a finding item importance set (hereinafter, referred to as importance set) 903. The importance set 903 contains pieces of information respectively indicating the degrees of importance of finding items such as a lesion 904, a size importance 905, a shape importance 906, a rate of calcification importance 907, a satellite lesions importance 908, . . . For example, information that indicates the degree of importance of each takes a value of any one of "high", "middle", and "low" defined in advance. Information that indicates a degree of importance may be any value that a user designates within a predetermined range or may be a binary value that indicates whether it is important. For example, information that indicates a degree of importance may be any one of discrete values, such as six values of "5", "4", "3", "2", "1", and "0", or may be a continuous value, such as any real value in a range from "0.0" to "1.0".

Figure 10:
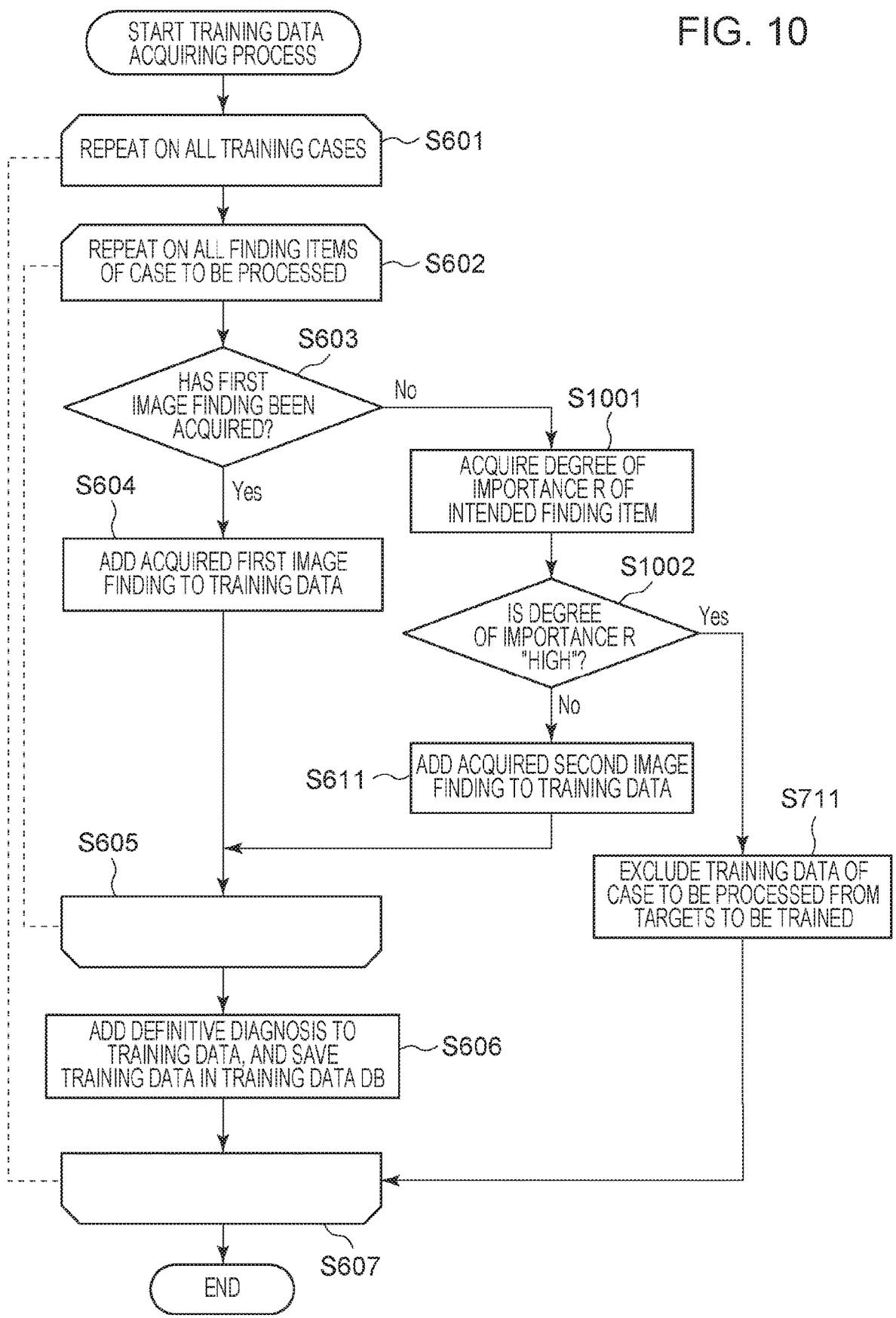
FIG. 10 is a flowchart that shows an example of a process that is executed by the information processing apparatus according to the fourth embodiment.

FIG. 10 is a flowchart that shows an example of a process that the training data acquiring unit 305 acquires training data in step S505 shown in FIG. 5.

Step S601, step S602, step S603, step S604, step S605, step S606, step S607, step S611, step S711, step S1001 and step S1002 make up a process that is executed on each of at least one case that is a candidate for training data, and make up a repeated process that is executed over all the cases acquired in step S501.

Step S602, step S603, step S604, step S605, step S611, step S711, step S1001 and step S1002 make up a process that is executed on each of the first image findings acquired for the i-th case, and make up a repeated process that is executed over all the finding items.

The training data acquiring unit 305 determines whether first image findings of the i-th case have been acquired (step S603). When the first image findings have not been acquired, the process proceeds to step S1001.

In step S1001, the importance acquiring unit (not shown) acquires a degree of importance R that is information indicating a degree of importance defined in advance for a finding item of an image finding by consulting the information list 900.

In step S1002, the importance acquiring unit (not shown) determines whether the degree of importance of the finding item is high. Specifically, the importance acquiring unit (not shown) determines, for example, whether the value of the degree of importance R is "high". When the degree of importance R is "high", the training data acquiring unit 305 does not use the i-th case as training data (step S711). On the other hand, when the degree of importance R is not "high" (No in S1002), second image findings acquired by analyzing a medical image of the case are used as training data (step S611).

When the i-th case is used as training data, the training data acquiring unit 305 adds a definitive diagnosis that is the diagnosed disease name of the case to training data and saves the definitive diagnosis in the training data DB 306 (step S606).

In the above-described example, the case where the information list 900 illustrated in FIG. 9 is determined in advance is described as an example. Alternatively, the information list 900 may be determined in advance or updated according to an inferred result of a disease name. For example, a user, the importance acquiring unit (not shown), the CAD apparatus 102, or another control unit (not shown) may infer a diagnosis while changing only the image finding of the rate of calcification in order of "high", "middle", "low", and "none" for a plurality of cases of "lung cancer", of which diagnoses are inferred as "lung cancer", and may determine the degree of importance R of the rate of calcification based on the percentage of cases whose inferred result has changed to other than "lung cancer". For example, the degree of importance R is set to "low" when the percentage of the changed cases is lower than 30%, set to "middle" when the percentage is higher than or equal to 30% and lower than 70%, and set to "high" when the percentage is higher than or equal to 70%. In other words, when the percentage is higher than or equal to 70%, it is estimated that the influence of an error in acquiring a finding on training of diagnostic inference is large, and an acquired case is not used for training in the above-described process of step S1002 and step S711. The information list 900 may be updated based on a result performed in the CAD apparatus 102 on a new case. For example, the degree of importance of a finding item whose disease name to be inferred changes or the probability of inference on a disease name changes a predetermined reference or more may be increased when inference is made while the value of a certain finding item input in a new case is replaced with "Null".

In the fourth embodiment, the example in which the degree of importance R is defined for each diagnosis is described. Alternatively, the degree of importance R may be defined for each finding item or may be defined in association with other clinical information related to diagnosis, such as a symptom. As in the case where the degree of importance R is "0" in step S1002, that is, when it is clear that the value of an image finding is independent of inference of the diagnosis, the value of the image finding may be null or may be a selected value.

With the information processing apparatus 101 according to the fourth embodiment, training data can be acquired based on first image findings and second image findings. Particularly, when some of first image findings input in existing data are lacking, the information processing apparatus 101 is able to compensate for the lacking data by using second image findings acquired through image analysis. When a finding item having a high degree of importance is lacking, the information processing apparatus 101 is able to exclude the case so as not to use the case as training data. Thus, machine training that is used in inference to be made by the CAD apparatus 102 can be accurately performed.

Fifth Embodiment

In a fifth embodiment, as well as the first embodiment, the information processing apparatus 101 that acquires training data for the CAD apparatus 102 that infers a diagnosis of a lung nodule shadow will be described. The information processing apparatus 101 according to the fifth embodiment acquires training data by using first image findings and second image findings according to the degree of confidence on the second image findings obtained by analyzing a medical image.

The system configuration including the information processing apparatus 101 according to the fifth embodiment, the hardware configuration and functional configuration of the information processing apparatus 101, the configuration of various pieces of information, which are acquired by the information processing apparatus 101, and the process that is executed by the information processing apparatus 101 are respectively similar to those of the first embodiment described with reference to FIG. 1, FIG. 2, FIG. 3, FIG. 4A to FIG. 4E, and FIG. 5, so the above description is incorporated herein, and the detailed description is omitted. Unless otherwise specified, like reference numerals denote the components described in the first embodiment.

The training data acquiring unit 305 of the information processing apparatus 101 according to the fifth embodiment includes an importance acquiring unit (not shown) and a confidence acquiring unit (not shown). The confidence acquiring unit (not shown) acquires a degree of confidence C that indicates how much the second image findings acquired by the image finding acquiring unit 304 are certain.

Figure 11:
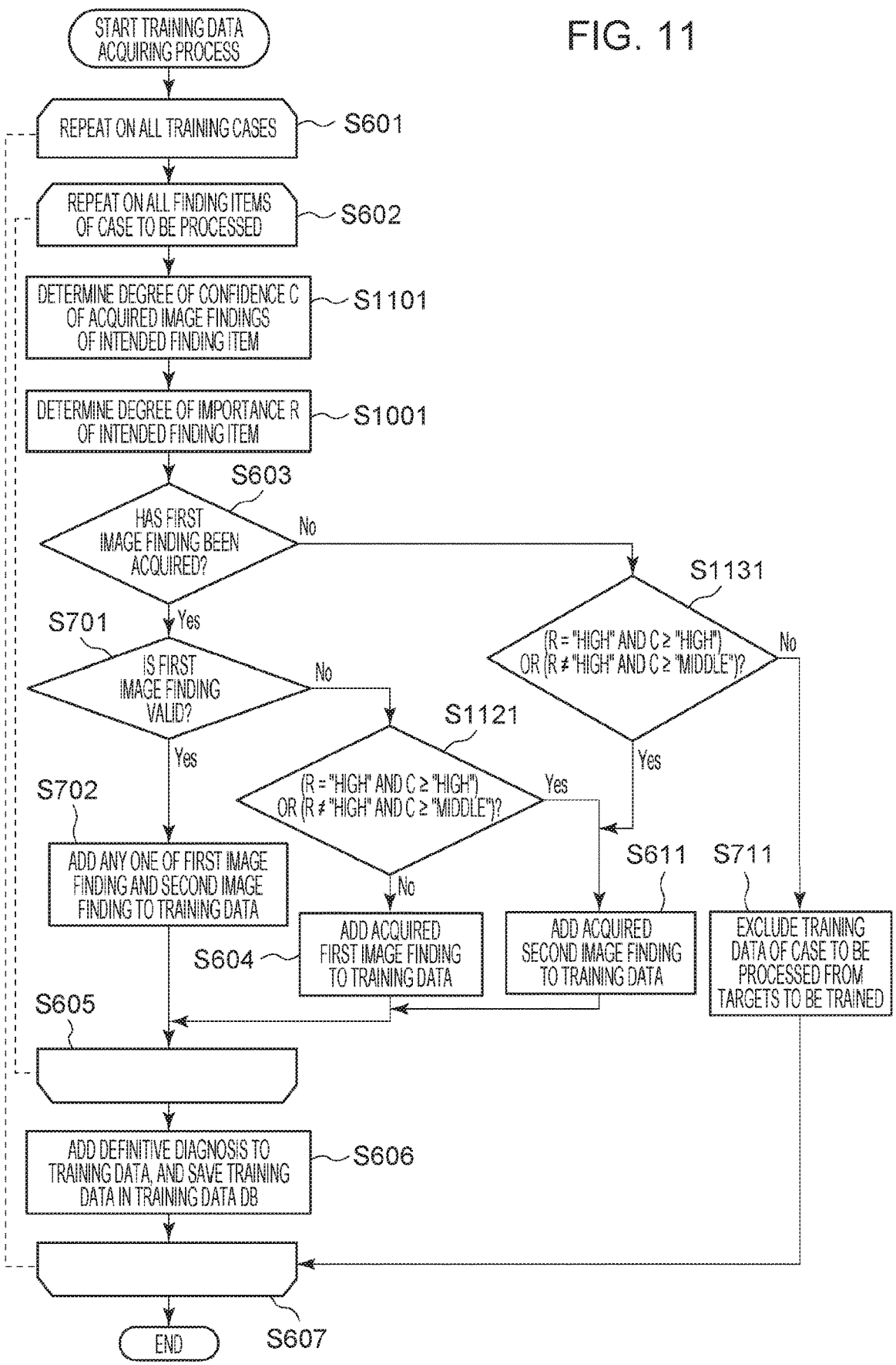
FIG. 11 is a flowchart that shows an example of a process that is executed by the information processing apparatus according to the fifth embodiment.

FIG. 11 is a flowchart that shows an example of a process that the training data acquiring unit 305 acquires training data in step S505 shown in FIG. 5.

Step S601, step S602, step S603, step S604, step S605, step S606, step S607, step S611, step S701, step S702, step S711, step S1001, step S1101, step S1121 and step S1131 make up a process that is executed on each of at least one case that is a candidate for training data, and make up a repeated process that is executed over all the cases acquired in step S501.

Step S602, step S603, step S604, step S605, step S611, step S701, step S702, step S711, step S1001, step S1101, step S1121 and step S1131 make up a process that is executed on each of the first image findings acquired for the i-th case, and make up a repeated process that is executed over all the finding items.

In the process of step S1101, the confidence acquiring unit (not shown) determines the degree of confidence C of each of the second image findings acquired in step S504. The degree of confidence C is, for example, a value that is acquired based on the probability of classification that the classifier that is used in the image finding acquiring unit 304 outputs, and is assumed to be based on an output value of a softmax function that is used in an output layer of CNN. For example, the degree of confidence C is "low" when the output value of the softmax function is less than 0.5, "middle" when the output value is greater than or equal to 0.5 and less than 0.8, and "high" when the output value is greater than or equal to 0.8.

The importance acquiring unit (not shown) acquires the degree of importance R of the finding item whose degree of confidence C has been acquired in step S1101 (step S1001). The training data acquiring unit 305 determines whether a first image finding has been acquired for the finding item (step S603). When the first image finding has not been acquired (No in S603), the process proceeds to step S1131.

In step S1131, the training data acquiring unit 305 determines whether the second image finding is used as training data based on the degree of importance R and the degree of confidence C. Specifically, the training data acquiring unit 305 determines, for example, whether the degree of importance R is "high" and the degree of confidence C is "high" or the degree of importance R is lower than or equal to "middle" and the degree of confidence C is higher than or equal to "middle". When the determined result of step S1131 is true (Yes in S1131), the second image finding acquired by analyzing a medical image of the case is used as training data (step S611). On the other hand, when the determined result of step S1131 is false (No in S1131), the training data acquiring unit 305 does not use the i-th case as training data (step S711).

When it is determined in step S603 that a first image finding has been acquired, the training data acquiring unit 305 determines whether the first image finding is used as training data (step S701). When it is determined that the first image finding is not used as training data (No in step S701), the process proceeds to step S1121.

A process related to determination that the training data acquiring unit 305 carries out in step S1121 is similar to the process related to determination in step S1131. The above description is incorporated herein, and the detailed description is omitted. When the determined result of step S1121 is true (Yes in S1121), the second image finding acquired by analyzing a medical image of the case is used as training data (step S611). On the other hand, when the determined result of step S1121 is false (No in S1121), the training data acquiring unit 305 adds the first image finding acquired in step S501 to the image findings set 454 of the training data 451-i (step S604).

When the above-described process has been completed on all the finding items of the i-th case and the i-th case is used as training data, the training data acquiring unit 305 adds a definitive diagnosis that is the diagnosed disease name of the case to training data and saves the definitive diagnosis in the training data DB 306 (step S606).

When the classifier of the image finding acquiring unit 304 has been obtained through machine training, the confidence acquiring unit (not shown) may, when the similarity between a medical image from which second image findings have has been acquired and a medical image used in machine training of the classifier is high, acquire a high degree of confidence C for a finding item of the second image findings. The confidence acquiring unit (not shown) may also acquire a high degree of confidence C for finding items associated with quantitative values that are obtained from an image, such as size and density. The confidence acquiring unit (not shown) may acquire a degree of confidence set for each finding item in advance. The confidence acquiring unit (not shown) may acquire a degree of confidence C based on the correct answer rate of image findings obtained through image analysis in a certain case whose correct image findings are known.

With the information processing apparatus 101 according to the fifth embodiment, training data can be acquired based on first image findings and second image findings. Particularly, when some of first image findings input in existing data are lacking, the information processing apparatus 101 is able to compensate for the lacking data by using second image findings acquired through image analysis. When first image findings have not been acquired and the degree of confidence C of second image findings corresponding to the first image findings is not high, the information processing apparatus 101 does not need to use the case as training data. When first image findings have been acquired and the degree of confidence C of second image findings is not high, the information processing apparatus 101 may use the first image findings as training data. When the degree of importance of a finding item is high, the information processing apparatus 101 may selectively use a case whose degree of confidence C of image analysis is high as training data. Thus, machine training that is used in inference to be made by the CAD apparatus 102 can be accurately performed.

Modifications

The case in which the CAD apparatus 102 makes an inference on a lung nodule and a chest disease is described in the above embodiments; however, the present invention is not limited thereto. For example, the CAD apparatus 102 may be an apparatus that makes an inference on another area or another disease, other than a lung nodule. The CAD apparatus 102 may be an apparatus that infers not only a disease but also a treatment strategy or a resemble case.

In the above-described embodiments, the case where training data is acquired based on first image findings acquired from, for example, an interpretation report and second image findings acquired based on an image feature vector of a medical image is described as an example; however, the present invention is not limited thereto. The CAD apparatus 102 may be configured to infer a disease name of pathology visualized in a medical image upon input of an image feature vector of the medical image. In this case, a case to be used as training data for the inferencer of the CAD apparatus 102 may contain an image feature vector in addition to or instead of image findings.

An example in which the information processing apparatus 101 acquires training data when the CAD apparatus 102 is configured to infer a disease name upon input of an image feature vector will be described. The information processing apparatus 101 acquires a first image feature vector by analyzing a medical image contained in a case whose disease name has been diagnosed in the past. A first image feature vector is an example of first information. However, it may be considered that a first image feature vector cannot be appropriately acquired depending on the status of a medical image input to the information processing apparatus 101 as a target to be analyzed. The status of a medical image is, for example, the quality and size of a medical image, or a subject that is visualized by the medical image. For example, there can be a case where an image feature vector for making an inference on a lung nodule cannot be acquired because medical information input to the information processing apparatus 101 does not contain a lung of a subject. According to a similar concept to those of the above-described embodiments, the information processing apparatus 101 selects whether a first image feature vector is used as training data based on, for example, the value of the first image feature vector, and a degree of importance determined in advance on the type of an image feature vector. When the first image feature vector is not used as training data, the information processing apparatus 101 acquires a second image feature vector. A second image feature vector is an example of second information. The information processing apparatus 101, for example, processes the medical image into an appropriate state to acquire an image feature vector of a type associated with the first image feature vector or enhances the degree of processing as compared to when the first image feature vector is acquired, then performs analysis again, and sets the acquired image feature vector as the second image feature vector. In another example, the information processing apparatus 101 acquires an image feature vector of a type associated with the first image feature vector in accordance with an algorithm different from the algorithm with which the first image feature vector is acquired.

When the CAD apparatus 102 is configured to infer a disease name upon input of an image feature vector as well, the information processing apparatus 101 is able to acquire training data based on first information and second information as in the case of the above-described first to fifth embodiments. At least any one of the information processing apparatus 101 and the CAD apparatus 102 may include a presenting unit (not shown) that presents a user with grounds for an inferred disease name from a case input to the CAD apparatus 102. The information processing apparatus 101 or the CAD apparatus 102 may include a conversion unit (not shown) that converts an image feature vector of a medical image input to the CAD apparatus 102 to image findings. The presenting unit (not shown) may present a user with information converted by the conversion unit (not shown) from an image feature vector to image findings as grounds for inference.

When first information and second information are compared with each other as in the case of the above-described embodiments and both the first information and the second information are image feature vectors, the comparison may be performed by using epidemiologic data or big data associated with image feature vectors in addition to the above-described example of comparison. For example, the range of the value of an image feature vector may be determined from information such as the age, sex, and anamnesis of a patient in a certain case, and the information processing apparatus 101 may determine which one of first information and second information is appropriate for training data based on the range.

In the above-described embodiments, the case where training data is acquired based on first image findings (first information) acquired from information such as an interpretation report and second image findings (second information) acquired by analyzing a medical image is described as an example; however, the present invention is not limited thereto. For example, at least one of first information and second information may be information other than image findings, contained in information, such as an interpretation report and an electronic health record. Information other than image findings, contained in an interpretation report or an electronic health record, is, for example, information such as the age or sex of a patient. Training data may be acquired based on not only first image findings and second image findings but also information other than the image findings. For example, the training data acquiring unit 305 does not need to use first information or second information, whose degree of reliability is considered to be low for the age or sex of a patient, as training data.

The training data acquiring unit 305 may determine whether first information or second information is used as training data based on a plurality of pieces of information acquired at multiple time points for the same patient. In other words, the information processing apparatus 101 may acquire training data based on time-series information of a specific patient, first information, and second information. The training data acquiring unit 305 acquires time-series information of an existing case and time-series information of a case that is a candidate for training data. For example, as for the finding item "size", the case where there is a high possibility that the size of a lung nodule increases in accordance with time-series information of an existing case will be considered as an example. As for the image finding "size" acquired for a case that is a candidate for training data, the information processing apparatus 101 compares image findings (first information and second information) acquired for the candidate case with image findings acquired in the past for the candidate case. When the image findings acquired for the candidate case indicate that the lung nodule has reduced as compared to the past image findings, the validity of the image findings acquired for the candidate case is determined to be low.

The present invention may also be implemented by a process in which a program that implements one or more functions of the above-described embodiments is supplied to a system or an apparatus via a network or a storage medium and one or more processors in a computer of the system or apparatus read and run the program. Alternatively, the present invention may be implemented by a circuit (for example, ASIC) that implements one or more functions.

The present invention may also be implemented by a process in which a program that implements one or more functions of the above-described embodiments is supplied to a system or an apparatus via a network or a storage medium and one or more processors in a computer of the system or apparatus read and run the program. Alternatively, the present invention may be implemented by a circuit (for example, ASIC) that implements one or more functions.

The information processing apparatus in each of the above-described embodiments may be implemented as a single apparatus or may be a form in which a plurality of apparatuses is combined so as to be communicable with each other and executes the above-described processes. The embodiment of the present invention encompasses both. A common server or a server group may execute the above-described processes. An information processing apparatus and a plurality of apparatuses that make up an information processing system may be configured to be communicable at a predetermined communication rate and do not need to be present in the same facility or same country.

The embodiments of the present invention encompass a mode in which a program of software that implements the functions of the above-described embodiments is supplied to a system or an apparatus and a computer of the system or apparatus reads and runs the code of the supplied program.

Therefore, to implement a process according to the embodiments with a computer, a program code itself that is installed in the computer is also one of the embodiments of the present invention. Based on a command contained in a program read by a computer, an OS, or the like, running on the computer executes part or all of actual processes, and the functions of the above-described embodiments can be implemented by the processes as well.

The embodiments of the present invention also encompass modes in which the above-described embodiments are combined as needed.

The present invention is not limited to the above-described embodiments. Various changes or modifications are applicable without departing from the spirit and scope of the present invention. Therefore, the following claims are attached to show the scope of the invention.

Training data for machine training is acquired based on information obtained as a result of a diagnosis and information not obtained as a result of the diagnosis, so machine training is further accurately performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus comprising:
one or more processors and one or more memories configured to:
acquire first information from text information of electronic case information, the first information being information on a feature of the case of a patient, the electric information being information including a first image finding and a diagnosis name, wherein the first image finding is information representing a feature of a disease, the diagnosis name is information of a disease name, and the first image finding and the diagnosis name are different type of information;
train a first classifier relationship between a medical image and a second image finding;
acquire second information by inputting one or more medical images of the patient that are associated with the first image finding to the first classifier, the second information being information on a physical feature of the patient, wherein the first classifier includes at least one of the following: an artificial neural network, a support vector machine, and a random forest, and wherein the first classifier is a classifier configured to output an image finding from an input of a medical image;
determine, based on a degree of coincidence between the first information and the second information, whether electronic case information is to be used as training data for machine training of a second classifier wherein when the degree of coincidence between the first information and the second information exceeds a predetermined reference value, the electric case information is determined to be used as the training data for the machine learning of the second classifier,
add the electronic case information which is determined to be used as the training data to a training dataset; and
train the second classifier using the training dataset, wherein the second classifier is a classifier based on supervised learning configured to output a diagnostic name from an input of an image finding, and wherein the first classifier and the second classifier are different from each other.

2. The information processing apparatus according to claim 1, wherein the one or more processors and the one or more memories are further configured to, when the first information does not correspond to the second information, determine that the electronic case information is not used as the training data.

3. The information processing apparatus according to claim 1, wherein the one or more processors and the one or more memories are further configured to determine, based on a degree of reliability of the second information, which one of the first information and the second information is used as the training data.

4. The information processing apparatus according to claim 1, wherein the one or more processors and the one or more memories are further configured to determine, based on a degree of importance in a diagnosis in terms of an item of the first information, whether the electronic case information is used as the training data.

5. The information processing apparatus according to claim 1, wherein the one or more processors are further configured to, in response to determining that the electronic case information is used as the training data, acquire the at least some of the electronic case information.

6. The information processing apparatus according to claim 1, wherein the one or more processors and the one or more memories are further configured to acquire the first information by extracting the first information from the electronic case information.

7. The information processing apparatus according to claim 6, wherein the one or more processors and the one or more memories are further configured to acquire the first information by retrieving an electronic interpretation report included in the electronic case information, and the one or more medical images of the patient correspond to the interpretation report.

8. The information processing apparatus according to claim 1, wherein the one or more processors and the one or more memories are further configured to acquire the first information from the text information of the electronic case information by performing morphological analysis and syntactic analysis on the text information.

9. The information processing apparatus according to claim 8, wherein the first information includes text information that represents one or more physical features of the patient.

10. The information processing apparatus according to claim 9, wherein the second information includes text information.

11. The information processing apparatus according to claim 10, wherein the one or more processors and the one or more memories are further configured to compare the first information and the second information and determine a degree of coincidence between the text information in the first information and the text information in the second information.

12. The information processing apparatus according to claim 1, wherein the one or more processors and the one or more memories are further configured to learn the second classifier,
wherein the information processing apparatus performs machine-learning on the second classifier using the training data.

13. The information processing apparatus according to claim 1, wherein the second classifier is a classifier on which machine-learning on a relationship between an image finding and a diagnostic name has been performed based on the training data.

14. The information processing apparatus according to claim 1, wherein the training data is a pair of an image finding based on the first information and the second information and a diagnosis name.

15. The information processing apparatus according to claim 1, wherein the first information and the second information are information about an image finding.

16. The information processing apparatus according to claim 1, wherein the second classifier is a classifier which is trained based on a rate of coincidence between the disease name that is an inferred result and the diagnosis name of the training dataset.

17. An information processing system comprising:
one or more processors and one or more memories configured to:
acquire first information from text information of electronic case information, the first information being information on a feature of the case of a patient, the electric information being information including a first image finding and a diagnosis name, wherein the first image finding is information representing a feature of a disease, the diagnosis name is information of a disease name, and the first image finding and the diagnosis name are different type of information;
train a first classifier relationship between a medical image and a second image finding;
acquire second information by inputting one or more medical images of the patient that are associated with the first image finding to the first classifier, the second information being information on a physical feature of the patient, wherein the first classifier includes at least one of the following: an artificial neural network, a support vector machine, and a random forest and wherein the first classifier is a classifier configured to output an image finding from an input of a medical image; and
determine, based on a degree of coincidence between the first information and the second information, whether electronic case information is to be used as training data for machine training of a second classifier wherein when the degree of coincidence between the first information and the second information exceeds a predetermined reference value, the electric case information is determined to be used as the training data for the machine learning of the second classifier;
train the second classifier using the training dataset, wherein the second classifier is a classifier based on supervised learning configured to output a diagnostic name from an input of an image finding, and wherein the first classifier and the second classifier are different from each other.

18. An information processing method comprising:
acquiring first information from text information of electronic case information, the first information being information on a feature of the case of a patient, the electric information being information including a first image finding and a diagnosis name, wherein the first image finding is information representing a feature of a disease, the diagnosis name is information of a disease name, and the first image finding and the diagnosis name are different type of information
training a first classifier relationship between a medical image and a second image finding;
acquiring second information by inputting one or more medical images of the patient that are associated with the first image finding to the first classifier, the second information being information on a physical feature of the patient, wherein the first classifier includes at least one of the following: an artificial neural network, a support vector machine, and a random forest and wherein the first classifier is a classifier configured to output an image finding from an input of a medical image; and
determining, based on a degree of coincidence between the first information and the second information, whether electronic case information is to be used as training data for machine training of a second classifier wherein when the degree of coincidence between the first information and the second information exceeds a predetermined reference value, the electric case information is determined to be used as the training data for the machine learning of the second classifier;
adding the electronic case information which is determined to be used as the training data to a training dataset; and
train the second classifier using the training dataset, wherein the second classifier is a classifier based on supervised learning configured to output a diagnostic name from an input of an image finding, and wherein the first classifier and the second classifier are different from each other.

19. A non-transitory computer-readable storage medium storing a program for causing a computer to execute the information processing method according to claim 18.

20. An information processing apparatus comprising:
one or more processors and one or more memories configured to:
acquire first information from text information of electronic case information, the first information being information on a feature of the case of a patient, the electric information being information including a first image finding and a diagnosis name, wherein the first image finding is information representing a feature of a disease, the diagnosis name is information of a disease name, and the first image finding and the diagnosis name are different type of information;
train a first classifier;
acquire second information by inputting one or more medical images of the patient that are associated with the first image finding to first classifier on which machine-learning on a relationship between a medical image and a second image finding has been performed, the second information being information on a physical feature of the patient, wherein the first classifier includes at least one of the following: an artificial neural network, a support vector machine, and a random forest, and wherein the first classifier is a classifier configured to output an image finding from an input of a medical image;
determine, based on a degree of coincidence between the first information and the second information, whether electronic case information is to be used as training data for machine training of a second classifier wherein when the degree of coincidence between the first information and the second information exceeds a predetermined reference value, the electric case information is determined to be used as the training data for the machine learning of the second classifier,
add the electronic case information which is determined to be used as the training data to a training dataset;
train the second classifier using the training dataset, wherein the second classifier is a classifier based on supervised learning configured to output a diagnostic name from an input of an image finding, and wherein the first classifier and the second classifier are different from each other; and infer a diagnosis name from an image finding which is acquired from a new case.

* * * * *